(12) United States Patent
Dubayle et al.

(10) Patent No.: US 11,197,831 B2
(45) Date of Patent: Dec. 14, 2021

(54) COMPOSITIONS COMPRISING AT LEAST ONE DISPERSED ACTIVE PRINCIPLE AND LIPID MICROCAPSULES

(71) Applicant: GALDERMA RESEARCH & DEVELOPMENT, Biot (FR)

(72) Inventors: Carole Dubayle, Mouans Sartoux (FR); Claire Mallard, Mougins (FR); Nicolas Atrux-Tallau, Antibes (FR)

(73) Assignee: GALDERMA RESEARCH AND DEVELOPMENT, Biot (FR)

( * ) Notice: Subject to any disclaimer, the term of this patent is extended or adjusted under 35 U.S.C. 154(b) by 0 days.

(21) Appl. No.: 15/577,857

(22) PCT Filed: May 27, 2016

(86) PCT No.: PCT/FR2016/051261
§ 371 (c)(1),
(2) Date: Nov. 29, 2017

(87) PCT Pub. No.: WO2016/193588
PCT Pub. Date: Dec. 8, 2016

(65) Prior Publication Data
US 2019/0091158 A1 Mar. 28, 2019

Related U.S. Application Data

(60) Provisional application No. 62/168,085, filed on May 29, 2015.

(51) Int. Cl.
| | | |
|---|---|---|
| *A61K 9/50* | (2006.01) | |
| *A61K 9/00* | (2006.01) | |
| *A61K 9/06* | (2006.01) | |
| *A61K 9/10* | (2006.01) | |
| *A61K 31/451* | (2006.01) | |
| *A61K 31/496* | (2006.01) | |
| *A61P 17/00* | (2006.01) | |
| *A61K 9/08* | (2006.01) | |
| *A61K 31/402* | (2006.01) | |

(52) U.S. Cl.
CPC .......... *A61K 9/5015* (2013.01); *A61K 9/0014* (2013.01); *A61K 9/06* (2013.01); *A61K 9/08* (2013.01); *A61K 9/10* (2013.01); *A61K 31/402* (2013.01); *A61K 31/451* (2013.01); *A61K 31/496* (2013.01); *A61P 17/00* (2018.01)

(58) Field of Classification Search
CPC .. A61K 31/192; A61K 31/203; A61K 31/402; A61K 9/0014; A61K 9/06; A61K 9/08; A61K 9/5015; A61K 2800/412; A61K 31/00; A61K 31/05; A61K 31/12; A61K 31/216; A61K 31/5575; A61K 31/573; A61K 47/10; A61K 47/14; A61K 47/24; A61K 8/11; A61K 8/37; A61K 8/375; A61K 8/553; A61K 8/671; A61K 8/86; A61K 9/10; A61K 9/107; A61K 31/7048; A61K 9/127; A61K 9/1617; A61K 2800/413; A61K 8/14; A61K 8/498; A61K 9/1075; A61K 9/14; A61K 9/5123; A61K 9/145; A61K 9/167; A61K 9/50; A61Q 19/00; A61P 17/00; A61P 11/06; A61P 17/06; A61P 17/08; A61P 17/10; A61P 19/02; A61P 1/02; A61P 29/00; A61P 35/04; A61P 37/00; A61P 37/02; A61P 3/00; A61P 3/04; A61P 3/06; A61P 3/10; A61P 9/00; A61P 9/10; A61P 9/12

See application file for complete search history.

(56) References Cited

U.S. PATENT DOCUMENTS

| | | | |
|---|---|---|---|
| 4,902,513 A | 2/1990 | Carvais | |
| 5,100,591 A * | 3/1992 | Leclef | A61K 9/1617 264/4.1 |
| 5,227,165 A * | 7/1993 | Domb | A01N 25/26 264/4.1 |
| 6,017,549 A | 1/2000 | Knight et al. | |
| 7,781,489 B2 | 8/2010 | Menegatti et al. | |
| 7,807,708 B2 * | 10/2010 | Biadatti | C07C 229/52 514/428 |
| 8,057,823 B2 | 11/2011 | Heurtault et al. | |
| 8,110,284 B2 | 2/2012 | Naigertsik et al. | |
| 8,309,121 B2 | 11/2012 | Net et al. | |
| 2005/0048088 A1 | 3/2005 | Zulu et al. | |
| 2007/0134276 A1 | 6/2007 | Menegatti et al. | |
| 2007/0184076 A1 | 8/2007 | Unger et al. | |
| 2008/0167375 A1 | 7/2008 | Weidner | |
| 2008/0193393 A1 | 8/2008 | Dayan | |

(Continued)

FOREIGN PATENT DOCUMENTS

| | | | | |
|---|---|---|---|---|
| FR | 2805761 A1 | 9/2001 | | |
| FR | WO2010/072958 A2 * | 7/2010 | ......... | A61K 31/7048 |
| IL | WO95/03829 * | 8/1994 | ............ | A61K 47/48 |
| WO | WO-91/07171 A1 | 5/1991 | | |
| WO | 9503829 A1 | 2/1995 | | |
| WO | WO-2006/066978 A1 | 6/2006 | | |

(Continued)

OTHER PUBLICATIONS

WO2010/072958A2 translation, Mazeau et al. (Year: 2010).*

(Continued)

*Primary Examiner* — Audrea B Coniglio

(74) *Attorney, Agent, or Firm* — Foley & Lardner LLP; Sunit Talapatra

(57) ABSTRACT

A composition is described that includes lipid microcapsules and at least one dispersed active principle. A method is also described for preparing the composition. Also described, is the use of the composition in the treatment of dermatological diseases.

26 Claims, 3 Drawing Sheets

(56) References Cited

U.S. PATENT DOCUMENTS

| | | | |
|---|---|---|---|
| 2009/0258065 A1* | 10/2009 | Baudonnet | A61K 9/0014 |
| | | | 424/452 |
| 2010/0098752 A1 | 4/2010 | Pinsky | |
| 2011/0195030 A1 | 8/2011 | Mumper et al. | |
| 2015/0125520 A1 | 5/2015 | Mallard | |
| 2016/0310439 A1 | 10/2016 | Mallard et al. | |

FOREIGN PATENT DOCUMENTS

| | | | | |
|---|---|---|---|---|
| WO | 2010063774 A1 | 6/2010 | | |
| WO | WO2010/063774 A1 * | 6/2010 | | C07D 211/22 |
| WO | 2010072958 A2 | 7/2010 | | |
| WO | WO-2010/113111 A1 | 10/2010 | | |
| WO | 2010133609 A2 | 11/2010 | | |
| WO | WO-2011/036234 A1 | 3/2011 | | |
| WO | WO-2013/178749 A1 | 12/2013 | | |
| WO | 2014140861 A2 | 9/2014 | | |
| WO | 2015082659 A1 | 6/2015 | | |

OTHER PUBLICATIONS

International Search Report and English translation dated Aug. 10, 2016 corresponding to International Patent Application No. PCT/FR2016/051261, 8 pages.

Liu et al. "Isotretinoin-loaded solid lipid nanoparticles with skin targeting for topical delivery." International journal of pharmaceutics 328.2 (2007): 191-195.

* cited by examiner

-□- Gel without capsules
-●- Gel IV/G-A11 of Example 3 (5% capric/caprylic acid triglycerides)
-○- Gel VI/G-A11 of Example 3 (20% capric/caprylic acid triglycerides)
-■- Reference cream

COMPOSITIONS COMPRISING AT LEAST ONE DISPERSED ACTIVE PRINCIPLE AND LIPID MICROCAPSULES

CROSS-REFERENCE TO PRIOR APPLICATIONS

This application is a National Stage of PCT/FR2016/051261, filed May 27, 2016, and designating the United States (published on Dec. 8, 2016, as WO 2016/193588 A1), which claims priority under 35 U.S.C. § 119 to U.S. Provisional Application No. 62/168,085, filed May 29, 2015, each hereby expressly incorporated by reference in its entirety and each assigned to the assignee hereof.

FIELD OF THE INVENTION

The present invention relates to a pharmaceutical composition. The invention also relates to the use of the composition to enhance the release and penetration of the active ingredient, and to the use of same for the treatment of various pathologies associated with the active ingredient used.

BACKGROUND OF THE INVENTION

Those skilled in the art are constantly confronted with difficulties in formulating active ingredients, particularly pharmaceutical active ingredients, on the one hand because of their potentially unfavorable solubility in the composition, and on the other because of their stability.

To reach the desired level of solubilization, it is sometimes necessary to incorporate a high concentration of solubilizer, usually excipients or solvents that are difficult to employ in formulation and particularly poorly tolerated at high concentration depending on the pathologies treated. Furthermore, once solubilized, the active ingredient, and the composition comprising same, must be stable.

However, it is known that the active ingredients incorporated in solubilized form are generally less stable in a composition than these same active ingredients incorporated in dispersed form in the composition.

Likewise, the active ingredients incorporated in solubilized form are often more irritating than these same active ingredients incorporated in dispersed form in the composition. On the other hand, it is more difficult for active ingredients incorporated in dispersed form to penetrate the skin compared with these same active ingredients in solubilized form in the composition.

Thus, there remains a need to formulate active ingredients in stable compositions with enhanced skin penetration of these active ingredients.

SUMMARY OF THE INVENTION

The problem which the present invention proposes to solve herein is thus to design a composition comprising at least one active ingredient dispersed in the composition, said composition being physically and chemically stable and able to provide good skin penetration of the dispersed active ingredient and good tolerance in the target pathology.

The Applicant surprisingly discovered that the presence of lipid microcapsules in a composition helps the dispersed active ingredient to penetrate the layers of the skin after application to the skin. The Applicant thus showed that, despite the presence of the active ingredient in dispersed form in the composition, the latter can penetrate the skin as well as if the active ingredient were in solubilized form. The Applicant further discovered, in a particularly surprising way, that it was not inevitably necessary for the contents of the oily core of the microcapsules to be good solvents of the active ingredient in order to obtain good penetration of the dispersed active ingredient.

The present invention thus relates to a pharmaceutical composition comprising at least one active ingredient dispersed in a pharmaceutically acceptable carrier, and microcapsules of micrometric size.

In the composition of the invention, and unlike the prior art, the active ingredient is not present in the lipid microcapsules and is in a pharmaceutically acceptable carrier. The composition of the invention notably aims to guarantee the stability of the active ingredient by integrating it into the composition in dispersed form and more particularly to enhance the skin penetration of said active ingredient despite its dispersed state. The composition of the invention is well tolerated with an advantageous sensory texture suited to the pathology to be treated.

In a preferred embodiment, the dispersed active ingredient is Trifarotene, (S)-4-(2,4-dihydroxyphenyl)-N-(1-phenylethyl)piperidine-1-carboxamide, or (S)—N-hydroxy-3-[4-(2-methyl-quinolin-4-ylmethoxy)-benzenesulfonylamino]-2-[4-(propane-2-sulfonyl)-piperazin-1-yl]-propionamide.

Particularly, the microcapsules of micrometric size contain an oily internal phase, and a nonpolymeric shell obtained from at least one lipid compound selected from amphiphilic lipids.

Preferably, the lipid compound constituting the shell of the microcapsules is selected from hydrogenated lecithins with a weight amount of phosphatidylcholine greater than 85%.

Preferably, the lipid compound constituting the shell of the microcapsules is present in an amount of between 0.01% and 10%, preferably between 0.05% and 5% by weight, and more preferentially between 0.1% and 1% by weight relative to the total weight of the composition.

Preferably, the oily internal phase of the microcapsules comprises at least one fatty substance that is liquid or semiliquid at ambient temperature (15-25° C. at atmospheric pressure). More preferentially, the oily internal phase is composed of triglycerides, of fatty acid esters, of polyethylene glycol ethers, or of dimethyl isosorbide.

In a preferred mode, the microcapsules are free of co-surfactant, of volatile organic solvent, or of polymer.

Particularly, the lipid microcapsules of micrometric size are dispersed in an aqueous phase. More particularly, the distribution profile of the microcapsules is such that 50% of the microcapsules have at least one mean size between 1 μm and 80 μm, preferentially between 1 μm and 50 μm, and more particularly between 1 μm and 20 μm.

A preferred subject-matter of the invention relates to a composition comprising 0.001% to 1% by weight of a dispersed active ingredient, preferably Trifarotene, (S)-4-(2,4-dihydroxyphenyl)-N-(1-phenylethyl)piperidine-1-carboxamide, or (S)—N-hydroxy-3-[4-(2-methyl-quinolin-4-ylmethoxy)-benzenesulfonylamino]-2-[4-(propane-2-sulfonyl)-piperazin-1-yl]-propionamide, in a pharmaceutically acceptable carrier, relative to the total weight of the composition, and lipid microcapsules composed of:

a. 0.1% to 5% of hydrogenated lecithin with a hydrogenated phosphatidylcholine content of greater than 85%; and b. 1% to 30% of oily and optionally non-oily fatty substances, preferably triglycerides, fatty acid esters, polyethylene glycol ethers, and dimethyl isosorbide.

In a particular embodiment, the pharmaceutically acceptable carrier of the composition of the invention is a gel.

In another particular embodiment, the pharmaceutically acceptable carrier of the composition of the invention is a cream.

Preferably, the composition of the invention is in a form suitable for topical administration.

Another subject-matter of the invention relates to the use of a composition as defined in the present invention to enhance the skin penetration of a dispersed active ingredient.

Another subject-matter of the invention also relates to the use of lipid microcapsules as defined in the present invention to enhance the skin penetration of a dispersed active ingredient.

The invention also relates to a composition as defined in the present application for use as a medicinal product.

The invention also relates to a composition as defined in the present application for use in the treatment of dermatological conditions. Preferably, the dermatological conditions are acne, ichthyosis, ichthyosiform conditions, palmoplantar hyperkeratosis, and psoriasis.

An additional subject-matter of the invention relates to a process for preparing a composition as defined in the present application comprising the following steps:
(i) preparing the primary emulsion by:
    a) preparing an oily phase heated to 75° C.,
    b) dispersing the lipid compound, and more preferentially the hydrogenated lecithin, in an aqueous phase, heated to 75° C.,
    c) incorporating the oily phase onto the aqueous phase already present in the apparatus with mixing at a speed of less than 16,000 rpm, and
    d) allowing the mixture to circulate until it returns to ambient temperature; and
(ii) incorporating the primary emulsion into the pharmaceutically acceptable carrier containing the dispersed active ingredient.

DETAILED DESCRIPTION OF THE INVENTION

Figure 1:
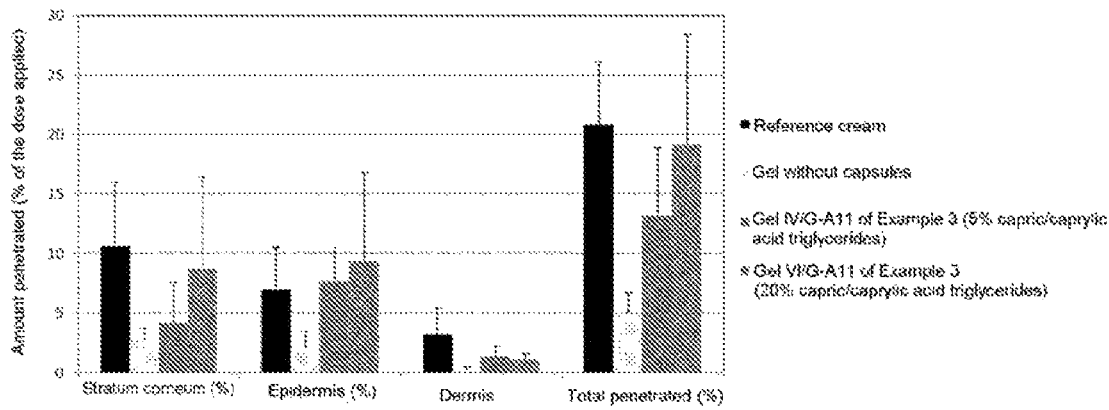
FIG. 1: Evaluation of the amount penetrated (% of the dose applied) in various skin compartments of Gels IV/G-A11 and VI/G-A11 of Example 3.

Many active ingredients, particularly pharmaceutical active ingredients, often present solubilization difficulties, thus limiting their incorporation into the carriers traditionally used and making it difficult to obtain a stable and effective composition. Furthermore, incorporation of the active ingredient in dispersed form often negatively affects the skin penetration of the active ingredient, and is not an ideal solution to the problem.

The Applicant thus discovered that the composition according to the present invention solved the above-mentioned problems. The composition according to the invention is thus able to contain, in addition to the microcapsules, at least one active ingredient in dispersed form in a pharmaceutically acceptable carrier, the active ingredient being known to those skilled in the art as presenting difficulties in terms of solubilization, of stability, of penetration, and/or of tolerance in solubilized form.

By way of non-limiting examples of active ingredients comprised in the compositions of the invention, particular mention may be made of:
    active ingredients that are difficult to solubilize and are stable in any type of medium, and in particular in highly aqueous medium, such as resorcinols and derivatives thereof, and notably the compound (S)-4-(2,4-dihydroxyphenyl)-N-(1-phenylethyl)piperidine-1-carboxamide (also called A2 in the present application),
    active ingredients that are difficult to solubilize and that require a high concentration of organic solvent, such as inhibitors of TNFα-converting enzyme (TACE) and notably the compound (S)—N-hydroxy-3-[4-(2-methyl-quinolin-4-ylmethoxy)-benzenesulfonylamino]-2-[4-(propane-2-sulfonyl)-piperazin-1-yl]-propionamide (also called A3 in the present application),
    active ingredients that, in solubilized form, are often poorly tolerated, and whose dispersion proves to be a favorable means of enhancing their tolerance, such as retinoids and preferably Trifarotene (also called A1 in the present application), and
    active ingredients that in solubilized form do not have a good controlled-release kinetics profile, such as retinoids and preferably Trifarotene.

The composition according to the invention comprises between 0.00001% and 5% of at least one dispersed active ingredient by weight relative to the total weight of the composition, preferably from 0.0001% to 3%, and preferentially the composition according to the invention contains from 0.001% to 1% of an active ingredient by weight relative to the total weight of the composition.

According to a preferred embodiment, the active ingredient is dispersed in the aqueous phase of the composition. But those skilled in the art will be able to adapt the ideal dispersion phase of the active ingredient in the composition according to the nature of the final composition and the effect sought.

The compositions of the invention enhance the penetration of dispersed active ingredients, by virtue of the presence of lipid microcapsules in the same pharmaceutically acceptable carrier. In the context of the present invention, said at least one active ingredient dispersed in a pharmaceutically acceptable carrier is outside the lipid microcapsules.

The present invention thus relates a composition comprising at least one active ingredient dispersed, in the presence of lipid microcapsules, in a cosmetically or pharmaceutically acceptable carrier.

According to the invention, the term "lipid microcapsules" is intended to mean lipid microcapsules having an oily internal phase and a nonpolymeric shell obtained from at least one lipid compound selected from amphiphilic lipids. Indeed, according to the present invention, the term "lipid microcapsules" is intended to mean a vesicular system of micrometric size (i.e., larger than a micron) consisting of a nonpolymeric lipid shell surrounding an oily core that is liquid or semiliquid at ambient temperature.

According to the present invention, the term "lipid microcapsules of micrometric size" is intended to mean more precisely lipid microsystems the size of which is preferentially between 1 μm and 100 rm.

According to a preferred mode of production, 50% of the lipid microcapsules have at least one mean size between 1 μm and 80 μm and preferentially between 1 μm and 50 μm. In a particularly preferred mode, the microcapsules according to the invention have a mean size between 1 μm and 20 μm.

The lipid microcapsules of micrometric size are present in the composition according to the invention in an amount of between 0.1% and 30% by weight relative to the total weight of the composition, preferably between 0.5% and 20%, and more particularly between 1% and 10%. Those skilled in the art will choose the amount of microcapsules suited to the level of penetration sought for a given dispersed active ingredient.

Each of the microcapsules consists of a lipid internal phase, or oily core, that is liquid or semiliquid at ambient temperature, and of a shell obtained from at least one lipid compound.

The term "oily core" or "lipid internal phase" refers to the internal phase of the lipid microcapsules containing a water-immiscible lipophilic compound or a water-immiscible mixture of lipophilic nature. Said lipid microcapsules and the process for obtaining same are notably disclosed in international patent applications WO 2015/082659 and WO 2015/082660.

One of the many advantages of the composition according to the invention is the use of lipid microcapsules of micrometric size, which does not require the use of the volatile organic solvents often used to form the shell. Lower concentrations, indeed an absence, of solvent compounds in the composition thus limit the risks of toxicity and of intolerance, and in particular of irritation.

According to the present invention, the composition comprises lipid microcapsules of micrometric size and not lipid microspheres. In contrast with the former, lipid microspheres are matrix particles, i.e., particles the entire mass of which is solid at ambient temperature. The lipid microcapsules of micrometric size according to the invention are particles whose core is composed of one or more fatty substances that are liquid or semiliquid at ambient temperature, and whose shell is lipid in nature and nonpolymeric. Indeed, the lipid microcapsules of micrometric size according to the invention require no polymer and thus no polymerization is observed in situ.

The Applicant has thus surprisingly discovered that compositions comprising at least one active ingredient in dispersed form, in the presence of lipid microcapsules of micrometric size, in a hydrophilic environment, not requiring the use of polymer or of volatile organic solvent, guaranteed the stability of the active ingredient and the skin penetration thereof even in dispersed form in the composition.

The lipid microcapsules of micrometric size according to the invention preferably consist of:
  a nonpolymeric shell obtained from at least one lipid compound, and
  at least one oily core.

The prior art (U.S. Pat. No. 8,057,823, FR 2 805 761 and WO2011/036234) discloses lipid capsules containing phosphatidylcholines but they are of nanometric size and require for their production the systematic presence of at least one nonionic hydrophilic co-surfactant that is an oxyethylene derivative of fatty alcohols and fatty acids.

Unlike the prior art, the present invention relates to lipid microcapsules of micrometric size containing exclusively phosphatidylcholines without any other additional lipophilic or hydrophilic co-surfactant.

The shell encapsulating the oily core that is liquid or semiliquid at ambient temperature is preferably composed of a nonpolymeric material that is rigid at ambient temperature and that has a high transition temperature or melting point. In order to be rigid at ambient temperature, the transition temperature or the melting point must be higher than 35° C., preferably higher than 40° C., and ideally higher than 45° C.

In the microcapsules according to the invention, the shell consists of at least one lipid compound of amphiphilic type. Preferentially, the shell consists of a single lipid compound, advantageously selected from amphiphilic lipids. More preferentially, the lipid compound is selected from the phospholipid family, and more specifically phosphatidylcholines or lecithins. Phosphatidylcholines or lecithins show good compatibility with the skin and have a very low irritant potential.

As lecithins that may be used, particular mention may be made of natural or synthetic or derived soybean or egg lecithins. The first type of lecithin is phosphatidylcholine (PC). Other types of lecithin exist, including phosphatidylglycerol, phosphatidylinositol, sphingomyelin and phosphatidylethanolamine.

Among the lecithins with a transition temperature higher than 35° C., more particular mention may be made of dipalmitoylphosphatidylcholine (DPPC), distearoylphosphatidylcholine (DSPC), dibehenylphosphatidylcholine (DBPC), palmitoylstearoylphosphatidylcholine (PSPC), palmitoylbehenylphosphatidylcholine (PSPC), stearoylbehenylphosphatidylcholine (SBPC), and any saturated lecithins with long fatty acid chains and derivatives thereof.

The lecithins notably used in the present invention are solid at ambient temperature, which promotes the formation of a semisolid interface around the liquid or semiliquid core.

The lipid microcapsules of micrometric size according to the invention contain more particularly a semisolid or solid interface between the internal phase and the aqueous continuous phase, by virtue of the use, as sole lipid compound, of a preferentially hydrogenated lecithin. More particularly, the hydrogenated lecithin used according to the invention has a high percentage of saturated phosphatidylcholine.

The term "high percentage" is intended to mean an amount of greater than 85% of hydrogenated (or saturated) phosphatidylcholine relative to the total weight of lecithin.

As lecithins preferentially used according to the invention, mention may be made of certain hydrogenated lecithins with a hydrogenated phosphatidylcholine content of greater than 85%, such as for example Lipoid® of grade P100-3, Phospholipon® of grade 90H sold by Lipoid, Epikuron® of grade 200 HS sold by Cargill, or Emulmetik® 950 sold by Lucas Meyer. Preferentially, the lecithin used as sole lipid compound is Phospholipon® 90H, the hydrogenated phosphatidylcholine content of which is greater than 90% and the transition temperature of which is about 54° C.

The lipid compound surrounding the liquid or semiliquid core as defined above is present in an amount of between 0.01% and 10% by weight, preferably between 0.05% and 5% by weight, and more preferentially between 0.1% and 1% by weight relative to the total weight of the composition.

In particular, the lipid microcapsule, and notably the shell, is free of any co-surfactant, in particular of lipophilic or hydrophilic co-surfactant.

The lipid microcapsules of micrometric size are notably free of volatile organic solvent.

In particular, the lipid microcapsules of micrometric size are free of polymer.

The term "lipophilic" refers, within the meaning of the present invention, to a compound that is soluble in a fatty substance that is liquid or semiliquid at ambient temperature. In other words, a lipophilic substance is liposoluble.

The composition of the internal phase is thus essential for the penetration of the active ingredient. The oily internal phase must of course be able to be compatible with the active ingredient to be delivered. The nature of the oily core and the concentration of microcapsules in the composition directly influence the level of penetration of the active ingredient and are thus selected so as to be best suited to the active ingredient.

The expression "compatible with the active ingredient in the oily phase" is intended to mean, within the meaning of the invention, that the active ingredient is chemically stable at ambient temperature for at least 24 h to 48 h.

The expression "fatty substance that is liquid or semiliquid at ambient temperature" refers, within the meaning of the present invention, to a water-immiscible lipophilic compound or a water-immiscible mixture of lipophilic nature.

More particularly, the liquid or semiliquid fatty substance may be a vegetable oil, a mineral oil, an animal oil, or a synthetic oil.

Likewise, the oily internal phase may also contain, in the presence of a liquid or semiliquid fatty substance, compounds of non-volatile organic solvent type, provided that the mixture of these compounds has a solubility for the active ingredient of interest of 0.02% or higher.

Among plant oils, mention may be made, in a non-limiting manner, of olive oil, almond oil, palm oil, soybean oil, sesame oil, canola oil, cotton seed oil, corn oil, safflower oil, castor oil, or sunflower oil.

Among mineral oils, mention may be made, in a non-limiting manner, of paraffin oils of various viscosities such as, for example, those sold by Exxon Mobil: Marcol 152®, Marcol 82® and Primol 352®.

Among animal oils, mention may be made, in a non-limiting manner, of lanolin, squalene, cod-liver oil, and squalane sold by Laserson under the trade name Cosbiol®.

Among synthetic oils, mention may be made, in a non-limiting manner, of triglycerides, the corresponding fatty acids and esters, carboxylic acid esters, fatty alcohols and corresponding esters, polyethylene glycol ethers, amides, silicone oils.

Among triglycerides and oils containing same, mention may be made, in a non-limiting manner, of octanoic acid triglycerides or caprylic/capric acid triglycerides such as those sold by Stearinerie Dubois or those sold under the name Miglyol® 810, 812 and 818 by Sasol.

Among fatty acids, mention may be made, in a non-limiting manner, of oleic acid sold by Croda under the name Super Refined Oleic Acid NF.

Among fatty acid esters, mention may be made, in a non-limiting manner, of diisopropyl adipate such as the commercial product Crodamol® DA sold by Croda or Schercemol DIA Ester® sold by Lubrizol, or cetearyl isononanoate sold under the name Cetiol SN® by BASF or apricot kernel oil PEG-6 esters sold under the name Labrafil M1944CS® by Gattefosse.

Among carboxylic acid esters, mention may be made, in a non-limiting manner, of ($C_{12-15}$) alkyl benzoate such as the commercial product Crodamol® AB sold by Croda, or propylene glycol caprylate sold under the name Capryol 90® by Gattefossé, or C12-C15 alkyl lactate sold by Ashland under the name Ceraphyl 41.

Among fatty alcohols, mention may be made, in a non-limiting manner, of octyldodecanol, octyldodecanol octanoate, and oleic alcohol sold under the name Novol by Croda.

Among polyethylene glycol ethers, mention may be made, in a non-limiting manner, of PPG-15 stearyl ether sold under the name Arlamol PS11E-LQ by Croda.

Among amides, mention may be made, in a non-limiting manner, of dimethyl capramide sold under the name Spectrasolv DMDA by Hallstar.

Among volatile and non-volatile silicones, mention may be made of dimethicones and cyclomethicones, such as those sold by Dow Corning under the trade names Q7-9120 Silicone Fluid® and ST-cyclomethicone 5-NF®.

Among compounds of non-volatile organic solvent type, mention may be made, in a non-limiting manner, of N-methyl-2-pyrrolidone, dimethyl isosorbide, diethylene glycol monoethyl ether sold under the name Transcutol HP by Gattefossé, and dimethyl sulfoxide sold under the name Procipient DMSO by Gaylord Chemical.

According to a preferred mode, the oily internal phase thus comprises at least one fatty substance, selected from triglycerides and oils containing same, fatty acid esters, polyethoxylated fatty acids, fatty alcohols and corresponding esters, polyethylene glycol ethers, amides and optionally a compound of non-volatile organic type, selected from diethylene glycol monoethyl ether and dimethyl sulfoxide.

In particular, those skilled in the art will select the suitable fatty substance(s) and non-volatile organic solvent(s) according to the active ingredient whose penetration must be enhanced.

According to a preferred embodiment, the preferred fatty substances for enhancing the skin penetration of Trifarotene are caprylic/capric acid triglycerides.

According to a preferred embodiment, the preferred fatty substances for enhancing the skin penetration of the compound (S)-4-(2,4-dihydroxyphenyl)-N-(1-phenylethyl)piperidine-1-carboxamide (A2) are a mixture of caprylic/capric acid triglycerides/dimethyl capramide, or a mixture of caprylic/capric acid triglycerides/diethylene glycol monoethyl ether, or caprylic/capric acid triglycerides.

According to a preferred embodiment, the preferred fatty substance for enhancing the skin penetration of the compound (S)—N-hydroxy-3-[4-(2-methyl-quinolin-4-yl-methoxy)-benzenesulfonylamino]-2-[4-(propane-2-sulfonyl)-piperazin-1-yl]-propionamide (A3) is a mixture of triglycerides/dimethylsulfoxide and preferably caprylic/capric acid triglycerides.

According to an embodiment, the lipid microcapsules contain:
- an oily internal phase comprising at least one fatty substance that is liquid or semiliquid at ambient temperature or one fatty substance/non-volatile organic solvent mixture selected from a triglyceride, a fatty acid ester, polyethylene glycol ethers, dimethyl capramide, diethylene glycol monoethyl ether, or dimethylsulfoxide;
- a nonpolymeric shell obtained from at least one lipid compound.

In the oily internal phase, the fatty substance or the lipophilic compound or the water-immiscible mixture of lipophilic nature will be present in an amount of between 50% and 99.997% by weight relative to the total weight of the internal phase; preferably in an amount of between 70% and 99.997% by weight relative to the total weight of the internal phase, preferably between 95% and 99.997%.

In the oily internal phase, the optional compound of non-volatile organic type is present in an amount of between 0% and 50% by weight relative to the total weight of the internal phase; preferably in an amount of between 0.1% and 25% by weight relative to the total weight of the internal phase, preferably between 0.5% and 20%.

In addition to said fatty substance(s) and said compound(s) of non-volatile organic type, the internal phase may also comprise one or more compounds, for instance antioxidants or preservatives.

By varying the amount of microcapsules present in the composition and the nature of the oily core, the present invention makes it possible to offer compositions with different sensory textures while providing the desired richness according to the pathologies to be treated.

The present invention also refers to a primary emulsion composed of lipid microcapsules of micrometric size dispersed in an aqueous phase.

The term "primary emulsion" thus refers to the lipid system composed of lipid microcapsules of micrometric size having a solid or semisolid interface dispersed in a continuous aqueous phase, said microcapsules containing an oily core, a shell obtained from a lipid compound, forming the semisolid or solid interface between the oily internal phase and the continuous aqueous phase. This primary emulsion is thus an oil-in-water-type emulsion.

Said oil-in-water-type primary emulsion according to the invention may be incorporated into a pharmaceutically acceptable carrier, such as a gel, a solution, or an emulsion such as a cream or a lotion.

In the primary emulsion according to the invention, the oily internal phase of the microcapsules is present in an amount of between 0.1% and 50% by weight relative to the total weight of the primary emulsion, preferably in an amount of between 0.5% and 35% by weight relative to the total weight of the primary emulsion.

In the primary emulsion according to the invention, the ratio between the oily internal phase and the amount of hydrogenated lecithin is between 5:1 and 10:1.

Preferably, this ratio in the emulsion is between 6:1 and 8:1, and preferentially is 7:1.

Furthermore, the ratio between water and the oily internal phase is between 1.25:1 and 5:1.

Preferably, this ratio between water and the oily internal phase is between 2:1 and 4:1, and preferentially is between 2:1 and 3:1.

In the primary emulsion, the microcapsules are dispersed in an aqueous phase. The continuous aqueous phase comprises water. Said water may be demineralized water, floral water, or natural thermal or mineral water.

Water may be present in a proportion of between 55% and 95% by weight relative to the total weight of the composition, preferably between 60% and 95% by weight.

The present invention thus also relates to a composition, notably a pharmaceutical composition, said composition comprising, in a pharmaceutically acceptable carrier, at least one dispersed active ingredient and the primary emulsion as defined above. The present invention thus relates to a pharmaceutical composition comprising, in a pharmaceutically acceptable carrier, at least one active ingredient dispersed in the presence of the primary emulsion composed of lipid microcapsules of micrometric size preferably consisting of:
- a nonpolymeric shell obtained from at least one lipid compound, and
- at least one oily core;

said lipid microcapsules of micrometric size being dispersed in an aqueous phase.

According to the invention, the term "composition" thus refers to at least one dispersed active ingredient and the primary emulsion, incorporated in a pharmaceutically acceptable carrier, such as an excipient or a mixture of excipients which may form a composition in the form of a gel, a solution, or an emulsion such as a cream or a lotion which is optionally sprayable.

The compositions according to the invention have the advantage of being chemically and physically stable.

According to the invention, the term "physical stability" refers to a composition of which the physical properties such as the organoleptic properties, the microcapsule size, the pH, and the viscosity are stable over time and under various temperature conditions: 4° C., ambient temperature, 40° C.

According to the invention, the term "chemical stability" refers to a composition in which the active ingredient is chemically stable over time, irrespective of the temperature condition: 4° C., ambient temperature, 40° C.

The term "ambient temperature" is intended to mean a temperature of between 15° C. and 25° C.

The present invention thus relates to a composition, notably a pharmaceutical composition, said composition comprising the dispersed active ingredient and the primary emulsion containing the lipid microcapsules of micrometric size as defined above in a pharmaceutically acceptable carrier, such as a gel, a solution, or an emulsion such as a cream or a lotion.

When the pharmaceutically acceptable carrier is a gel, the primary emulsion is dispersed in an aqueous phase which comprises at least one gelling agent. Preferably, the aqueous phase comprises the dispersed active ingredient.

Said gelling agent may be a cellulose-based derivative selected from semisynthetic cellulose-based gelling agents.

The gelling agent may also be selected from natural gums, in particular xanthan gum (known for example under the name Satiaxane and sold by Cargill), starch and derivatives thereof, cross-linked polyacrylic acid polymers, for instance carbomers, such as Carbopol 980, Carbopol Ultrez 10 and from alkyl derivatives thereof, for instance copolymers of acrylates/C10-30 alkyl acrylate, such as Carbopol ETD2020, Pemulen TR1, Pemulen TR2, carboxyvinyl polymers, polyvinylpyrrolidones and derivatives thereof, polyvinyl alcohols.

The gelling agent may also be selected from emulsifying polymers such as Sepigel 305 consisting of a polyacrylamide/C13-C14 isoparaffin/laureth-7 mixture, or Simulgel® 600PHA or Sepineo® P600, namely sodium acryloyldimethyltaurate copolymer/isohexadecane/polysorbate 80. These two products are sold by Seppic.

When the pharmaceutically acceptable carrier is a solution, the primary emulsion is dispersed in a carrier composed of an aqueous phase. Preferably, the aqueous phase comprises the dispersed active ingredient.

The expression "aqueous phase which constitutes the pharmaceutically acceptable carrier" is intended to mean any aqueous phase as defined previously in the present invention.

When the pharmaceutically acceptable carrier is a cream or a lotion, the primary emulsion is dispersed in a carrier composed of an aqueous phase and of a fatty phase optionally comprising a surfactant or an emulsifier.

In the case of pharmaceutical carriers in cream or lotion form, the composition according to the invention thus comprises a fatty phase. Said fatty phase may comprise, for example, plant oils, mineral oils, animal oils, synthetic oils or silicone oils, and mixtures thereof.

Preferably, when the carrier of the composition according to the invention is a cream or a lotion, the emulsion is in the form of an oil-in-water (O/W) emulsion. Said emulsion may optionally comprise at least one emulsifier.

The cream or the lotion according to the invention also comprises an aqueous phase.

The expression "aqueous phase which constitutes the pharmaceutically acceptable carrier, alone or in an emulsion" is intended to mean any aqueous phase as defined previously in the present invention.

The composition according to the invention may also contain, in the primary emulsion or in the pharmaceutically acceptable carrier, one or more additives or combinations of additives, such as:
 preservatives;
 penetration enhancers;
 stabilizers;
 humectants;
 moisture regulators;
 pH regulators;
 osmotic pressure modifiers;
 chelators;
 UV-A and UV-B filters; and
 antioxidants.

Needless to say, those skilled in the art will take care to select the ingredients of the pharmaceutically acceptable carrier and, in particular, the aqueous phases, the fatty phases, the emulsifiers, and also the optional compound(s) to be added to these compositions, such that the advantageous properties intrinsically associated with the present invention are not, or are not substantially, adversely affected by the choice of the ingredients. According to a preferred embodiment, the active ingredient is dispersed in the aqueous phase of the composition. But those skilled in the art will be able to adapt the ideal dispersion phase of the active ingredient in the composition according to the nature of the final composition and the effect sought.

The composition according to the invention thus comprises, in a pharmaceutically acceptable carrier, on a weight basis relative to the total weight of the composition, 0.00001% to 5% of an active ingredient dispersed in the presence of microcapsules composed of:
 a) a nonpolymeric shell obtained from 0.01% to 10% of lipid compound selected from amphiphilic lipids;
 b) an oily core composed of from 0.1% to 50% of fatty substance and optionally of compounds of non-volatile organic solvent type as long as the mixture remains lipophilic and liquid or semiliquid at ambient temperature.

The expression "active ingredient dispersed in the presence of microcapsules" is intended to mean that the active ingredient is dispersed in the pharmaceutically acceptable carrier in the presence of microcapsules, and not that it is comprised in the microcapsules.

The composition according to the invention thus preferably comprises in a pharmaceutically acceptable carrier, on a weight basis relative to the total weight of the composition, 0.0001% to 3% of an active ingredient dispersed in the presence of microcapsules composed of:
 a) 0.1% to 5% of lipid compound selected from amphiphilic lipids, preferably hydrogenated lecithin;
 b) 1% to 30% of fatty substance and of compounds of non-volatile organic solvent type, preferably triglycerides, fatty acid esters, polyethylene glycol ethers, dimethyl isosorbide.

In a preferred mode according to the invention, the composition comprises in a pharmaceutically acceptable carrier, on a weight basis relative to the total weight of the composition, 0.001% to 1% of an active ingredient in the presence of microcapsules composed of:
 a) 0.1% to 5% of hydrogenated lecithin with a hydrogenated phosphatidylcholine content of greater than 85%;
 b) 1% to 30% of fatty substance and of compounds of non-volatile organic solvent type, preferably triglycerides, fatty acid esters, polyethylene glycol ethers, dimethyl isosorbide.

The pharmaceutical composition that may be used according to the invention is intended for treating the skin and may be administered via the topical, parenteral or oral routes.

Via the oral route, the pharmaceutical composition may be in liquid or pasty form, and more particularly in the forms of gel capsules, coated tablets, or syrups.

Via the parenteral route, the composition may be in the form of suspensions for perfusion or for injection.

Preferably, the composition is in a form suitable for topical administration. The term "via the topical route" is intended to mean application to the skin, the mucous membranes, the hair, or the scalp.

Via the topical route, the composition may be in liquid or pasty form, and more particularly in the form of creams, milks, pomades, impregnated pads, syndets, wipes, gels, sprays, foams, lotions, sticks, shampoos, or washing bases.

Another subject-matter of the invention is a process for preparing the compositions according to the invention. The preparation processes for the composition of the invention and the microparticles are notably disclosed in international patent applications WO 2015/082659 and WO 2015/082660, incorporated herein by reference.

The process according to the invention does not involve phase inversion phenomena characterized by a phase inversion temperature (PIT) (used notably in patents FR 2 805 761 and FR 2 840 531), and therefore does not require temperature increase and decrease cycles.

The process according to the invention does not use a high-pressure homogenizer (HPH) and therefore does not require a pre-homogenization step.

The process according to the invention thus has the simultaneous advantages of not having successive heating and cooling cycles, of not using volatile organic solvent or polymer, and of not requiring a step of gelling the emulsion or a pre-homogenization step.

The process as presented according to the invention and proposed for producing the lipid microcapsules of micrometric size uses equipment that allows high-shear emulsification.

Various devices can be used, for instance high-shear rotor/stator type mixers, such as a POLYTRON® (Kinematica) or the Magic LAB® (IKA). In a manner likewise alternative to the rotor/stator, sonication may be used with, for example, a Branson probe. Whatever the type of equipment used, the process consists in producing a primary emulsion, which is then diluted in a pharmaceutically acceptable carrier.

This primary emulsion makes it possible to vary the mode of introduction of the lipid compound, preferably hydrogenated lecithin, which may be totally introduced into the oily phase (100% oily phase) or into the aqueous phase (100% aqueous phase) or introduced in various ratios, for instance a 50:50 ratio, into the oily phase and into the aqueous phase.

1—Preparation of the Primary Emulsion:

The production of the primary emulsion comprises 3 steps:
Preparation of the aqueous phase
Preparation of the oily phase
Mixing of the aqueous phase and the oily phase Preparation of the aqueous phase and of the oily phase is dependent on the choice of the dispersion mode of the lipid compound, preferably hydrogenated lecithin:
100% in the aqueous phase, or
100% in the oily phase, or
50% in the aqueous phase and 50% in the oily phase.

a) Preparation of the primary emulsion with 100% dispersion of the lipid compound, preferably hydrogenated lecithin, in the aqueous phase:

Preparation of the Aqueous Phase:

In a container suitable for containing all of the primary emulsion, the hydrogenated lecithin used is dispersed in all of the aqueous phase heated to roughly 75° C., using a high-shear rotor/stator type mixer such as an ULTRA-TURRAX® (IKA), a POLYTRON® (Kinematica) or the Magic LAB® (IKA), with stirring between 5,000 and 10,000 rpm, for a defined period of time not to exceed 30 minutes. A preservative and an antioxidant may be added to this phase.

Preparation of the Oily Phase:

In a suitable container and using a magnetic bar, the compounds of the lipophilic mixture will be mixed and heated to 75° C. A preservative and an antioxidant may be added to this phase.

b) Preparation of the primary emulsion with 100% dispersion of the lipid compound, preferably hydrogenated lecithin, in the oily phase:

Preparation of the Aqueous Phase:

In a container suitable for containing all of the primary emulsion, all of the aqueous phase is heated to 75° C. A preservative and an antioxidant may be added to this phase.

Preparation of the Oily Phase:

In a suitable container and using a magnetic bar, the compounds of the lipophilic mixture will be mixed and heated to 75° C. A preservative and an antioxidant may be added to this phase.

The lipid compound used, preferably hydrogenated lecithin, is dispersed in this oily phase still at about 75° C., using a high-shear rotor/stator type mixer such as an ULTRA-TURRAX® (IKA) or a POLYTRON© (Kinematica), with stirring between 5,000 and 10,000 rpm, for a defined period of time not to exceed 30 minutes.

c) Preparation of the primary emulsion with 50% of the hydrogenated lecithin dispersed in the aqueous phase and 50% in the oily phase:

Preparation of the Aqueous Phase:

In a container suitable for containing all of the primary emulsion, all of the aqueous phase is heated to 75° C. About half of the lipid compound used, preferably hydrogenated lecithin, is dispersed in this aqueous phase still heated to roughly 75° C., using a high-shear rotor/stator type mixer such as an ULTRA-TURRAX© (IKA), a POLYTRON© (Kinematica) or the Magic LAB© (IKA), with stirring between 5,000 and 10,000 rpm, for a defined period of time not to exceed 30 minutes. A preservative and an antioxidant may be added to this phase.

Preparation of the Oily Phase:

In a suitable container and using a magnetic bar, the compounds of the lipophilic mixture will be mixed and heated to 75° C. The other portion of the lipid compound, preferably hydrogenated lecithin, is dispersed in this oily phase still heated to about 75° C., using a high-shear rotor/stator type mixer such as an ULTRA-TURRAX® (IKA) or a POLYTRON© (Kinematica), with stirring between 5,000 and 10,000 rpm, for a defined period of time not to exceed 30 minutes. A preservative and an antioxidant may be added to this phase.

Once the aqueous phase and the oily phase have been prepared, they are mixed by incorporation of the oily phase into the aqueous phase. The procedure is dependent on the type of apparatus used. Three types of apparatus are preferentially used for mixing the two phases resulting in the primary emulsion according to the invention: the process with a POLYTRON®, the process with a Magic LAB® (IKA) and the process with a sonication probe. According to the various types of stirrers, the emulsion is produced as described:

Process with a POLYTRON® with temperature regulation at 75° C.:
Incorporation of the oily phase onto the aqueous phase gently, with stirring between 5,000 and 10,000 rpm.
Once the incorporation has been achieved, stirring at a higher speed for at least 30 minutes.

Process with a Magic LAB© (IKA) with temperature regulation at 75° C.:
Simultaneous incorporation of the aqueous phase and of the oily phase in the apparatus with stirring at a speed of less than 16,000 rpm if the lipid compound, preferably hydrogenated lecithin, was 100% dispersed in the fatty phase.
Incorporation of the oily phase onto the aqueous phase already present in the apparatus with stirring at a speed of less than 16,000 rpm if the lipid compound, preferably hydrogenated lecithin, was 100% dispersed in the aqueous phase.
Once the incorporation has been achieved, the mixture is allowed to circulate until it returns to ambient temperature.

Process with the sonication probe with temperature regulation fixed below 50° C.:
Incorporation of the oily phase onto the aqueous phase rapidly, at an ultrasound amplitude fixed at 80 microns,
The mixture is left under these conditions for several tens of seconds.

2—Preparation of the Final Composition According to the Invention

The primary emulsion previously obtained is introduced into a previously prepared pharmaceutically acceptable carrier containing the dispersed active ingredient, of solution, cream, lotion or gel type.

In the case of a gel containing mainly only water and a gelling agent, the gelling step is carried out instantaneously at the end of the production of the primary emulsion:
Remove a predetermined amount of primary emulsion and
Incorporate it gently into a previously prepared gel, with gentle stirring. The stirring may be generated using a deflocculating paddle attached to a stirring motor of IKA or Rayneri type. Gentle stirring corresponds to a speed that produces a homogeneous gel after 20 minutes without generating excessive aeration of the formulation, for example a speed of around 200 rpm.

Alternatively, to prepare a composition of gel type according to the invention, an amount of primary emulsion may be removed and then diluted in one part water. This mixture is then thickened by adding a gelling agent.

The process for preparing the compositions according to the invention comprises the following steps:
(i) preparing the primary emulsion by:
(a) preparing the oily phase,
(b) preparing the aqueous phase,
(c) dispersing the lipid compound in the oily phase obtained in (a) or in the aqueous phase obtained in (b) or partly in each of the oily and aqueous phases,
(d) heating the two oily and aqueous phases separately to about 75° C.,
(e) mixing with stirring the oily and aqueous phases obtained at the conclusion of step (d),
(ii) incorporating the composition obtained in the preceding step into a pharmaceutically acceptable carrier comprising at least one dispersed active ingredient.

The Applicant surprisingly discovered that the mode of introduction of the lipid compound, and more particularly of the hydrogenated lecithin, has an influence on the stability over time of the microcapsules dispersed in the pharmaceutically acceptable carrier.

Preferably, the lipid compound is introduced either 100% into the oily phase, or 100% into the aqueous phase, depending on the nature of the oily core selected to enhance the penetration of the active ingredient dispersed in the pharmaceutically acceptable carrier.

More preferentially, the hydrogenated lecithin is introduced either 100% into the oily phase, or 100% into the aqueous phase, depending on the nature of the oily core selected. In a preferred mode according to the invention, the preferred apparatus is the Magic LAB® (IKA).

In a preferred mode according to the invention, the preferred dispersion mode of the lipid compound, and more preferably of the hydrogenated lecithin, is 100% in the fatty phase, in the case of the use of oily compounds of triglyceride and acid ester type, for instance diisopropyl adipate.

In another preferred mode according to the invention, the preferred dispersion mode of the lipid compound, and more preferably of the hydrogenated lecithin, is 100% in the aqueous phase, in particular in the case of the use of oily compounds of polyethylene glycol ether type, for instance PPG-15 stearyl ether.

In particular, those skilled in the art will choose the suitable oily core according to the active ingredient dispersed in the final composition, in order to best enhance the penetration thereof.

Those skilled in the art will also adapt the preferred dispersion mode of the lipid compound, and more preferably of the hydrogenated lecithin.

In one of the preferred modes, the process for preparing a composition according to the invention comprises the following steps:
(i) preparing the primary emulsion by:
a) preparing an oily phase heated to 75° C.,
b) preparing an aqueous phase, heated to 75° C.,
c) simultaneously incorporating the aqueous phase and the oily phase in the apparatus with stirring at a speed of less than 16,000 rpm,
d) once the incorporation has been achieved, allowing the mixture to circulate until it returns to ambient temperature;
(ii) incorporating the primary emulsion into the pharmaceutically acceptable carrier containing the dispersed active ingredient.

In one of the preferred modes, the process for preparing a composition according to the invention comprises the following steps:
(i) preparing the primary emulsion by:
a) preparing an oily phase heated to 75° C.,
b) dispersing the lipid compound, and more preferably the hydrogenated lecithin, in an aqueous phase, heated to 75° C.,
c) incorporating the oily phase onto the aqueous phase already present in the apparatus with stirring at a speed of less than 16,000 rpm,
d) once the incorporation has been achieved, allowing the mixture to circulate until it returns to ambient temperature;
(ii) incorporating the primary emulsion into the pharmaceutically acceptable carrier containing the dispersed active ingredient Preferably, these preparation processes are carried out in the absence of volatile organic solvent.

As previously indicated, the composition according to the invention comprises, in a pharmaceutically acceptable carrier, at least one active ingredient dispersed in the presence of lipid microcapsules of micrometric size dispersed in an aqueous phase, said lipid microcapsules of micrometric size containing an oily internal phase and a nonpolymeric shell obtained from at least one lipid compound selected from amphiphilic lipids.

In a preferred mode according to the invention, the composition containing the microcapsules increases the penetration of the dispersed active ingredient. Preferentially, the skin penetration of an active ingredient dispersed in the presence of lipid microcapsules relative to that obtained with an active ingredient dispersed without microcapsules is higher than a factor of 2 to 50, preferably of 2 to 20.

The present invention thus relates to the use of the composition according to the invention to enhance the skin penetration of a dispersed active ingredient.

In another mode, the present invention relates to the use of the composition to enhance the skin penetration kinetics profile of a dispersed active ingredient. As shown in the following non-limiting examples (see Ex. 6 and FIG. 2), the penetration kinetics profile of the active ingredient dispersed in the composition according to the invention approaches over long periods of time that observed with a composition in which the active ingredient is solubilized.

The particular advantage of the composition according to the invention containing the dispersed active ingredient is that the exposure is decreased over shorter periods of time (5 h), which thus induces better tolerance.

The composition according to the invention containing the lipid microcapsules thus confers better penetration of the dispersed active ingredient, relative to a similar composition without microcapsules, and approaches the level of penetration of the active ingredient in its solubilized form while showing a kinetics profile that improves tolerance.

The composition according to the invention may be used as a medicinal product.

In particular, another subject-matter of the invention is the composition as previously defined for use in the treatment of dermatological conditions, notably human dermatological conditions, as defined below:
1) dermatological conditions associated with a keratinization disorder relating to cell differentiation and proliferation, notably for treating common acne, comedonal acne, polymorphic acne, acne rosacea, nodulocystic acne, acne conglobata, senile acne, secondary acne such as solar acne, drug-related acne, or occupational acne;
2) keratinization disorders, in particular ichthyoses, ichthyosiform conditions, lamellar ichthyoses, Darier's disease, palmoplantar keratoderma, leukoplakia, *Pityriasis rubra* pilaris and leukoplakia-like conditions, cutaneous or mucosal (oral) lichen;
3) dermatological conditions with an inflammatory immuno-allergic component, with or without a cell proliferation disorder, and in particular all forms of psoriasis, whether cutaneous, mucosal, or ungual, and even psoriatic arthritis, or else atopic dermatitis and the various forms of eczema;
4) skin disorders caused by exposure to UV radiation, and also for repairing or combating skin aging, whether photo-induced or chronological aging, or for reducing actinic keratoses and pigmentations, or any pathological conditions associated with chronological or actinic aging, such as xerosis, pigmentations, and wrinkles;
5) any condition associated with benign dermal or epidermal proliferations, whether or not they are of viral origin, such as common warts, flat warts, molluscum contagiosum and epidermodysplasia verruciformis, or oral or florid papillomatoses;
6) dermatological disorders such as immune dermatoses, for instance lupus erythematosus, bullous immune diseases, and collagen diseases, such as scleroderma;
7) stigmata of epidermal and/or dermal atrophy induced by local or systemic corticosteroids, or any other form of cutaneous atrophy;
8) cicatrization disorders, or for preventing or repairing stretch marks, or else for promoting cicatrization;
9) in the treatment of any condition of fungal origin at the cutaneous level, such as tinea pedis and tinea versicolor;
10) pigmentation disorders, such as hyperpigmentation, melasma, hypopigmentation, or vitiligo;
11) cutaneous or mucosal cancerous or precancerous conditions, such as actinic keratoses, Bowen's disease, in situ carcinomas, keratoacanthomas and skin cancers such as basal cell carcinoma (BCC), squamous cell carcinoma (SCC), and cutaneous lymphomas such as T lymphoma.

Preferentially, the invention relates to the composition for use in the treatment of acne, ichthyosis, ichthyosiform conditions, palmoplantar hyperkeratosis, or psoriasis.

In other words, the invention relates to the composition according to the invention for use as medicinal product in the treatment of dermatological conditions, notably human dermatological conditions, as previously defined.

Particularly preferably, the composition according to the invention is used for treating acne, ichthyosis, ichthyosiform conditions, palmoplantar hyperkeratosis, rosacea, or psoriasis.

Various formulations of compositions comprising lipid microcapsules in a pharmaceutically acceptable carrier and compositions with at least one active ingredient dispersed in the presence of lipid microcapsules will now be given, as illustration and with no limiting nature.

EXAMPLES

Example 1: Primary Emulsions Containing the Lipid Microcapsules Before Dilution

By using the preparation processes cited above and according to the dispersion mode of the hydrogenated lecithin as defined previously in the present description, lipid microcapsules were produced with an oily core containing an oil (primary emulsions I to VI) or a mixture of oils (primary emulsions VII to IX).

The compositions of the primary emulsions I to IX are thus as follows:

| Ingredients | Composition (% w/w) | | | | | |
| --- | --- | --- | --- | --- | --- | --- |
|  | I | II | III | IV | V | VI |
| Diisopropyl adipate | 27.89 | — | — | — | — | — |
| PPG-15 stearyl ether | — | 27.89 | 27.89 | — | — | — |
| Capric/caprylic acid triglycerides | — | — | — | 27.89 | 27.89 | 27.89 |
| Hydrogenated lecithin | 4.04 | 4.04 | 4.04 | 4.04 | 4.04 | 4.04 |
| Propyl paraben | 0.56 | 0.56 | 0.14 | 0.56 | — | 0.14 |
| Methyl paraben | 1.12 | 1.12 | 0.28 | 1.12 | — | 0.28 |
| Benzoic acid | — | — | — | — | 0.279 | — |
| Purified water | q.s. | q.s. | q.s. | q.s. | q.s. | q.s. |
|  | 100 | 100 | 100 | 100 | 100 | 100 |

| Ingredients | VII | VIII | IX |
| --- | --- | --- | --- |
| Dimethyl capramide | 5.58 | — | — |
| Diethylene glycol monoethyl ether | — | 11.16 | — |
| Dimethyl sulfoxide | — | — | 5.58 |
| Capric/caprylic acid triglycerides | 22.31 | 16.73 | 22.31 |
| Hydrogenated lecithin | 4.04 | 4.04 | 4.04 |
| Propyl paraben | — | — | 0.28 |
| Methyl paraben | — | — | 0.56 |
| Benzoic acid | 0.139 | 0.139 | — |
| Butyl hydroxytoluene | — | — | 0.1 |
| Purified water | q.s. | q.s. | q.s. |
|  | 100 | 100 | 100 |

Example 2: Solubility and Stability Data for Trifarotene in Various Fatty Substances The solubility and the stability of the active ingredient were evaluated by liquid chromatography coupled to a UV detector (HPLC-UV).

| INCI name (trade name) | Maximum solubility (% w/w) (AT) | Stability |
|---|---|---|
| Propylene glycol monocaprylate (Capryol ® 90) | 0.802 | 6 months AT/40° C. |
| Propylene glycol monolaurate (Lauroglycol ® FCC) | 0.296 | 6 months AT/40° C. |
| Diisopropyl adipate (Schercemol Dia Ester) | 0.297 | 6 months AT/40° C. |
| PPG-15 stearyl ether (Arlamol PS11E-LQ) | 0.292 | 6 months AT/40° C. |
| Macrogol oleate (Labrafil ® M1944CS) | 0.156 | 6 months AT/40° C. |
| Octyldodecanol (Eutanol ® G) | 0.137 | Unstable |
| Propylene glycol dicaprylate/dicaprate (Myritol ® PC) | 0.069 | Unstable |
| Alkyl (C12-15) benzoate (Crodamol AB) | 0.026 | Not monitored |
| Capric/caprylic acid triglycerides (Miglyol ® 812N) | 0.019 | 6 months AT/40° C. |
| Sweet almond oil | 0.011 | 6 months AT/40° C. |
| Mineral oil | 0.0001 | Not monitored |

Following the results of this solubility and stability study, it is noted that propylene glycol monocaprylate, propylene glycol monolaurate, diisopropyl adipate, PPG-15 stearyl ether, and macrogol oleate are suitable for solubilizing Trifarotene.

Following these results, diisopropyl adipate and PPG-15 stearyl ether are the preferred solvents selected to be inserted in the oily core in the microcapsules.

Capric/caprylic acid triglycerides remain the oily compound selected from the poorest solvents to be inserted in the oily core in the microcapsules.

Example 3: Examples of Compositions of Gel Type According to the Invention Containing Trifarotene (A1) Dispersed in the Presence of Lipid Microcapsules Produced from the Primary Emulsions of Example 1

In order to produce compositions of gel type I/G-A1$_1$, II/G-A1$_1$, II/G-A1$_1$, IV/G-A1$_1$ and VI/G-A1$_1$ according to the invention, an amount of corresponding primary emulsion prepared according to Example 1 was taken and diluted in a gel base.

To obtain 100 grams of gel containing about 5% of microencapsulated oil, 17.784 grams of primary emulsion is added to a formulation containing 0.01% of dispersed micronized Trifarotene (gels I/G-A1$_1$, IUG-A1$_1$ and IV/G-A1$_1$).

To obtain 100 grams of gel containing about 20% of microencapsulated oil, 71.71 grams of primary emulsion is added to a formulation containing 0.01% of dispersed micronized Trifarotene (gels III/G-A1$_1$ and VI/G-A1$_1$).

Primary emulsions I, II, III, IV and VI lead to the gel compositions I/G-A1$_1$, II/G-A1$_1$, III/G-A1$_1$, IV/G-A1$_1$ and VI/G-A1$_1$, respectively, described in the table below. Examples of compositions of gel type obtained according to the invention are thus as follows:

| Ingredients | Composition (% w/w) | | | | |
|---|---|---|---|---|---|
| | I/G-A1$_1$ | II/G-A1$_1$ | III/G-A1$_1$ | IV/G-A1$_1$ | VI/G-A1$_1$ |
| Micronized Trifarotene | 0.01 | 0.01 | 0.01 | 0.01 | 0.01 |
| Diisopropyl adipate | 4.96 | — | — | — | — |
| PPG-15 stearyl ether | — | 4.96 | 20 | — | — |
| Capric/caprylic acid triglycerides | — | — | — | 4.96 | 20 |
| Hydrogenated lecithin | 0.72 | 0.72 | 2.90 | 0.72 | 2.90 |
| Methyl paraben | 0.2 | 0.2 | 0.2 | 0.2 | 0.2 |
| Propyl paraben | 0.1 | 0.1 | 0.1 | 0.1 | 0.1 |
| Sodium acryloyldimethyltaurate copolymer/isohexadecane/polysorbate 80 | 4 | 4 | 4 | 4 | 4 |
| Sodium docusate | 0.05 | 0.05 | 0.05 | 0.05 | 0.05 |
| Disodium edetate | 0.1 | 0.1 | 0.1 | 0.1 | 0.1 |
| Glycerol | 4 | 4 | 4 | 4 | 4 |
| Propylene glycol | 4 | 4 | 4 | 4 | 4 |
| Poloxamer P124 | 0.2 | 0.2 | 0.2 | 0.2 | 0.2 |
| Lactic acid (q.s. pH 3.5-4) | q.s. pH | q.s. pH | q.s. pH | q.s. pH | q.s. pH |
| Purified water | q.s. 100 | q.s. 100 | q.s. 100 | q.s. 100 | q.s. 100 |

Example 4: Characterization of the Compositions of Example 3 of Gel Type According to the Invention, According to the Lipophilic Compound Used and the Percentage of Microencapsulated Lipophilic Mixture or Mixture of Lipophilic Nature In the present examples, the equipment that was used to produce the primary emulsions is the Magic LAB® (IKA).

The preferred dispersion mode for the hydrogenated lecithin with diisopropyl adipate is 100% in the fatty phase.

The preferred dispersion mode for the hydrogenated lecithin with PPG-15 stearyl ether is 100% in the aqueous phase.

The preferred dispersion mode for the hydrogenated lecithin with capric/caprylic acid triglycerides is 100% in the fatty phase.

The gel compositions I/G-A1$_1$, II/G-A1$_1$ and IV/G-A1$_1$ contain 0.01% of dispersed micronized Trifarotene, in the presence of about 5% of microencapsulated oil.

| Primary emulsion/Oil | Characterizations | Results |
|---|---|---|
| | Composition I/G-A1$_1$ | |
| I/ Diisopropyl adipate | Macroscopic observation | White gel |
| | Microscopic observation | Capsules of micrometric size and presence of Trifarotene crystals |
| | pH | 4.99 |
| | Viscosity RV, S06, 10 rpm | 66,300 cP |
| | Composition II/G-A1$_1$ | |
| II/ PPG-15 stearyl ether | Macroscopic observation | White gel |
| | Microscopic observation | Capsules of micrometric size and presence of Trifarotene crystals |
| | pH | 4.67 or 4.76 |
| | Viscosity RV, S06, 10 rpm | 64,900 cP |
| | Composition IV/G-A1$_1$ | |
| IV/ Capric/caprylic acid triglycerides | Macroscopic observation | White gel |
| | Microscopic observation | Capsules of micrometric size and presence of Trifarotene crystals |
| | pH | 4.82 |
| | Viscosity RV, S06, 10 rpm | 60,300 cP |

The gel compositions III/G-A1$_1$ and VI/G-A1$_1$ contain 0.01% of dispersed micronized Trifarotene, in the presence of about 20% of microencapsulated oil.

| Primary emulsion/Oil | Characterizations | Results |
|---|---|---|
| | Composition III/G-A1$_1$ | |
| III/ PPG-15 stearyl ether | Macroscopic observation | White gel |
| | Microscopic observation | Capsules of micrometric size and presence of Trifarotene crystals |
| | pH | 5.02 |
| | Viscosity RV, S06, 2.5 rpm | 330,000 cP |
| | Composition VI/G-A1$_1$ | |
| VI/ Capric/caprylic acid triglycerides | Macroscopic observation | White gel |
| | Microscopic observation | Capsules of micrometric size and presence of Trifarotene crystals |
| | pH | 4.82 |
| | Viscosity RV, S06, 2.5 rpm | 370,000 cP |

Example 5: Stability Study of the Gels of Example 4 According to the Lipophilic Compound Used and According to the Percentage of Microencapsulated Lipophilic Mixture or Mixture of Lipophilic Nature Gel Obtained from Composition I/G-A1$_1$ of Example 3 (4.96% Diisopropyl Adipate)

| Characterizations | Storage conditions | Stability at 3 months |
|---|---|---|
| Macroscopic appearance | T0 | White gel |
| | AT | IDEM T0 |
| | 4° C. | IDEM T0 |
| | 40° C. | IDEM T0 |
| Microscopic appearance | T0 | Capsules of micrometric size and presence of Trifarotene crystals |
| | AT | IDEM T0 |
| | 4° C. | IDEM T0 |
| | 40° C. | IDEM T0 |
| pH Viscosity RV, S06, 10 rpm | T0 | pH = 4.99 66,300 cP |
| | AT | pH = 4.88 59,100 cP |
| | 40° C. | pH = 4.62 58,400 cP |
| Conclusions | | Physically stable gel |

Gel Obtained from Composition II/G-A1$_1$ of Example 3 (4.96% PPG-1.5 Stearyl Ether)

| Characterizations | Storage conditions | Stability at 3 months |
|---|---|---|
| Macroscopic appearance | T0 | White gel |
| | AT | IDEM T0 |
| | 4° C. | IDEM T0 |
| | 40° C. | IDEM T0 |
| Microscopic appearance | T0 | Capsules of micrometric size and presence of Trifarotene crystals |
| | AT | IDEM T0 |
| | 4° C. | IDEM T0 |
| | 40° C. | IDEM T0 |
| pH Viscosity RV, S06, 10 rpm | T0 | pH = 4.76 64,900 cP |
| | AT | pH = 4.70 59,400 cP |
| | 40° C. | pH = 4.74 51,400 cP |
| Trifarotene assay Rec %/T0 | AT | 101.8 |
| | 40° C. | 102.5 |
| Conclusions | | Physically and chemically stable gel |

Gel Obtained from Composition IV/G-A1$_1$ of Example 3 (4.96% Capric/Caprylic Acid Triglycerides)

| Characterizations | Storage conditions | Stability at 3 months |
|---|---|---|
| Macroscopic appearance | T0 | White gel |
| | AT | IDEM T0 |
| | 4° C. | IDEM T0 |
| | 40° C. | IDEM T0 |
| Microscopic appearance | T0 | Capsules of micrometric size and presence of Trifarotene crystals |
| | AT | IDEM T0 |
| | 4° C. | IDEM T0 |
| | 40° C. | IDEM T0 |

| Characterizations | Storage conditions | Stability at 3 months |
|---|---|---|
| pH | T0 | pH = 4.82 |
| Viscosity | | 60,300 cP |
| RV, S06, 10 rpm | AT | pH = 4.92 |
| | | 57,500 cP |
| | 40° C. | pH = 4.81 |
| | | 54,500 cP |
| Trifarotene assay | AT | 100.9 |
| Rec %/T0 | 40° C. | 98.7 |
| Conclusions | | Physically and chemically stable gel |

Gel Obtained from Composition III/G-A1$_1$ of Example 3 (20% PPG-15 Stearyl Ether)

| Characterizations | Storage conditions | Stability at 3 months |
|---|---|---|
| Macroscopic | T0 | White gel |
| appearance | AT | IDEM T0 |
| | 4° C. | IDEM T0 |
| | 40° C. | IDEM T0 |
| Microscopic | T0 | Capsules of micrometric size and presence of Trifarotene crystals |
| appearance | AT | IDEM T0 |
| | 4° C. | IDEM T0 |
| | 40° C. | IDEM T0 |
| pH | T0 | pH = 5.02 |
| Viscosity | | 330,000 cP |
| RV, S06, 2.5 rpm | AT | pH = 4.68 |
| | | 307,000 cP |
| | 40° C. | pH = 4.62 |
| | | 269,000 cP |
| Trifarotene assay | AT | 100.6 |
| Rec %/T0 | 40° C. | 101.1 |
| Conclusions | | Physically and chemically stable gel |

Gel Obtained from Composition VI/G-A1$_1$ of Example 3 (20% Capric/Caprylic Acid Triglycerides)

| Characterizations | Storage conditions | Stability at 3 months |
|---|---|---|
| Macroscopic | T0 | White gel |
| appearance | AT | IDEM T0 |
| | 4° C. | IDEM T0 |
| | 40° C. | IDEM T0 |
| Microscopic | T0 | Capsules of micrometric size and presence of Trifarotene crystals |
| appearance | AT | IDEM T0 |
| | 4° C. | IDEM T0 |
| | 40° C. | IDEM T0 |
| pH | T0 | pH = 4.82 |
| Viscosity | | 136,000 cP |
| RV, S06, 2.5 rpm | AT | pH = 4.86 |
| | | 110,000 cP |
| | 40° C. | pH = 4.91 |
| | | 90,000 cP |
| Trifarotene assay | AT | 101.7 |
| Rec %/T0 | 40° C. | 99.9 |
| Conclusions | | Physically and chemically stable gel |

The results show that gels are obtained which are stable at three months at ambient temperature and at 40° C. in the presence of a dispersed active ingredient, namely Trifarotene.

Example 6: Study of In Vitro Skin Penetration Kinetics of Dispersed Trifarotene in Eel Formulations in the Presence of Microcapsules Produced According to Example 1

Study Conditions:

In this study, the formulations were applied for 24 hours to the skin surface. After the application, Trifarotene is quantified at several points in time (1 h, 3 h, 6 h, 8 h and 24 h) in the various skin compartments: stratum corneum, epidermis, dermis, and receiving liquid according to a validated bioanalysis method performed by positive electrospray ionization tandem mass spectrometry, using a Xevo system (Waters). The quantification limit for Trifarotene is 0.01 ng/mL. The LC/MS/MS conditions developed made it possible to detect up to 0.1% of the dose applied in each compartment (dose not absorbed, stratum, epidermis, dermis, and receiving liquid).

The details of the skin application are given in the table below.

| Skin: 3 donors, 2 samples per donor | |
|---|---|
| Source | Whole human abdominal skin |
| Franz cells | 1 cm$^2$ |
| Receiving liquid volume | 3 mL |
| Barrier function | Evaluated by determination of insensible water loss, acceptable unless contraindication |

Reference cream containing 100 µg/g solubilized Trifarotene

Reference gel containing 100 µg/g dispersed micronized Trifarotene

Gel no. IV/G-A1$_1$ Example 3 containing 100 µg/g micronized Trifarotene dispersed in the presence of 5% microencapsulated lipophilic compound (capric/caprylic acid triglycerides)

-continued

| Skin: 3 donors, 2 samples per donor | |
|---|---|
| Gel no. VI/G-A1₁ Example 3 containing 100 µg/g micronized Trifarotene dispersed in the presence of 20% microencapsulated lipophilic compound (capric/caprylic acid triglycerides) | |
| | Application |
| Application | 5 mg/cm² |
| Amount of active ingredient applied | 380-436 ng/cm² |
| Number of cells per formulation | 30 (6 cells per exposure time) |
| Number of donors per formulation | 3 |
| Exposure time | 1 h, 3 h, 6 h, 8 h and 24 h |
| | Sample assay |
| Washing of donor compartment and wiping | "Excess"/Dose not absorbed |
| First strip | |
| Stratum corneum (2-15 strips max) | Total skin |
| Epidermis | |
| Dermis | |
| Receiving liquid | Dose absorbed |
| | LC/MS analysis |
| Quantification limit | 0.01 ng/mL |

The reference cream formula is an oil-in-water cream containing 0.01% solubilized Trifarotene in the internal fatty phase.

The reference gel formula is a gel containing 0.01% dispersed Trifarotene the base composition of which is identical to those of gels IV/G-A1₁ and VI/G-A1₁ of Example 3. The reference gel is free of microcapsules.

| Ingredients/INCI names | Composition (% w/w) |
|---|---|
| Micronized Trifarotene | 0.01 |
| Methyl paraben | 0.2 |
| Propyl paraben | 0.1 |
| Sodium acryloyldimethyltaurate copolymer/isohexadecane/ polysorbate 80 | 4 |
| Sodium docusate | 0.05 |
| Disodium edetate | 0.1 |
| Glycerol | 4 |
| Propylene glycol | 4 |
| Poloxamer P124 | 0.2 |
| Lactic acid (q.s. pH 3.5-4) | q.s. pH |
| Purified water | q.s. 100 |

Results:

The results presented in FIG. 1 show the amount penetrated as a percentage of the dose applied (% of the dose applied) according to the various skin compartments after 24 h of exposure. The total amount penetrated corresponds to the amount of active ingredient assayed in the various skin compartments (stratum corneum, epidermis, dermis) and the receiving liquid.

Figure 2:
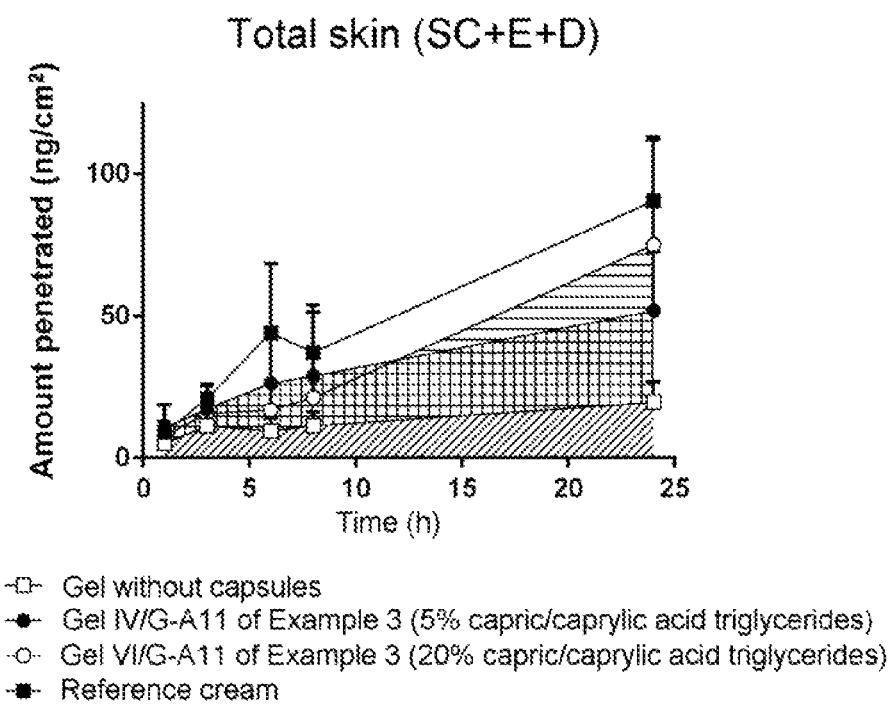
FIG. 2: Penetration profile of Gels IV/G-A11 and VI/G-A11 of Example 3 over 24 hours.

The results presented in FIG. 2 show the penetration profile of Trifarotene with the various formulations tested over 24 hours.

Figure 3:
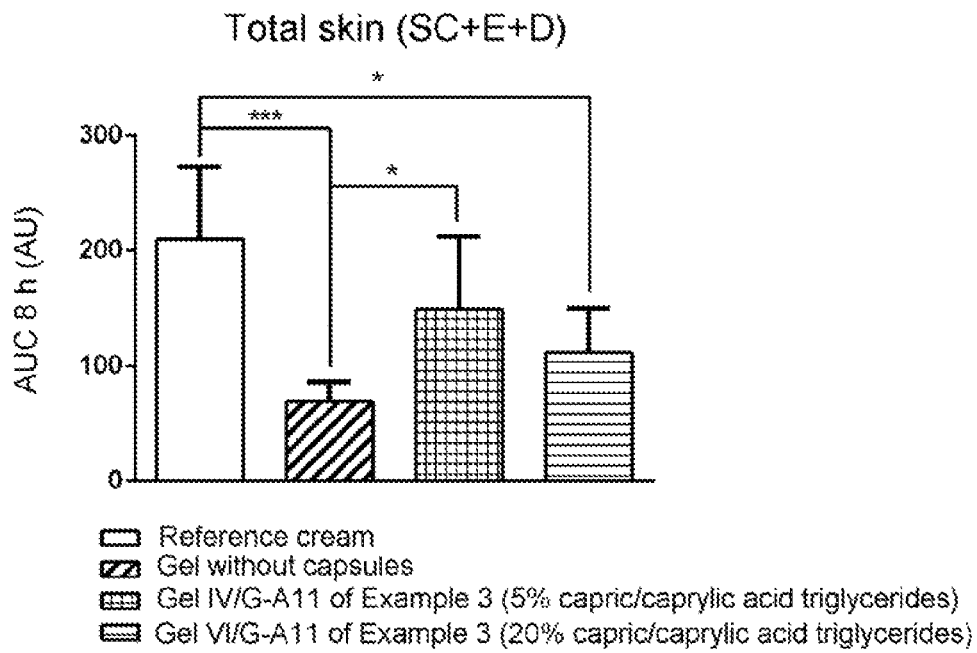
FIG. 3: Representation of the areas under the curve (AUCs) after 8 hours of Gels IV/G-A11 and VI/G-A11 of Example 3.
Figure 4:
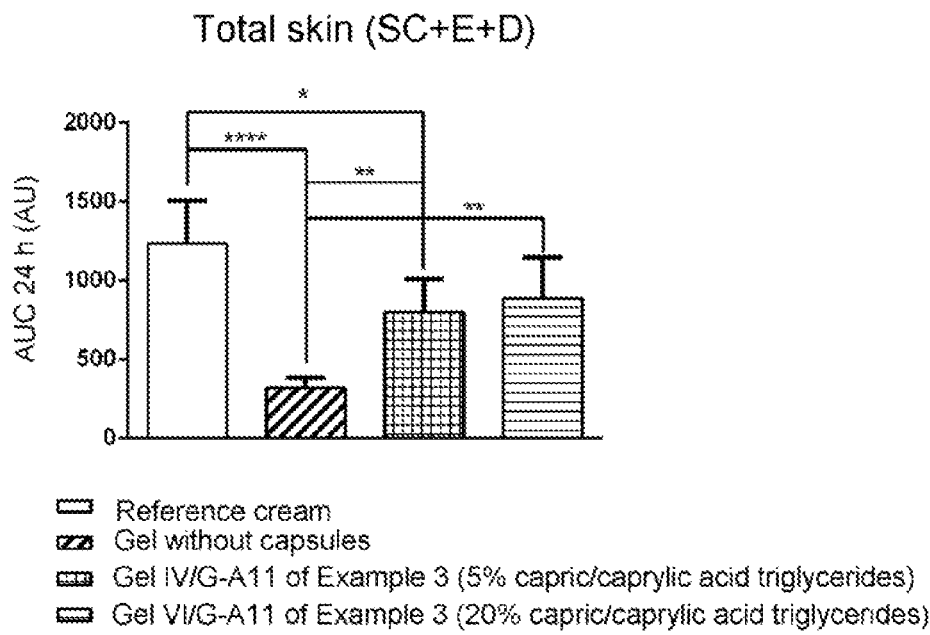
FIG. 4: Representation of the areas under the curve (AUCs) after 24 hours of Gels IV/G-A11 and VI/G-A11 of Example 3.

FIGS. 3 and 4 present the areas under the curve (AUCs) calculated respectively after 8 hours, corresponding to the shortest exposure times, and after 24 hours, corresponding to the longest exposure times. The AUCs were calculated for each kinetics (n=6). They were then statistically compared by one-way ANOVA followed by Dunnett's test.

The AUC values at 8 hours and 24 hours, respectively, are as follows:

| AUC values | Reference creme | Gel without capsules | Gel IV/G-A1₁ (5% oil) | Gel VI/G-A1₁ (20% oil) |
|---|---|---|---|---|
| AUC 8 h | | | | |
| Mean | 209.60 | 69.11 | 149.20 | 111.80 |
| Standard deviation | 63.43 | 16.98 | 63.47 | 38.16 |
| AUC 24 h | | | | |
| Mean | 1234 | 318.3 | 797.3 | 886.3 |
| Standard deviation | 272.5 | 63.57 | 211.4 | 259.1 |

Conclusions:

According to FIG. 1, irrespective of the formulation tested, the skin distribution of Trifarotene is essentially located in the stratum corneum and the epidermis, and more moderately in the dermis. In the presence of microcapsules, the total amount of Trifarotene penetrated is significantly higher than the reference gel in which Trifarotene is dispersed alone without the presence of microcapsules.

For the reference gel comprising dispersed Trifarotene without microcapsules, the total amount penetrated is about 4.93% at 24 h.

For the reference cream comprising solubilized Trifarotene, the total amount penetrated is about 20.83%.

For the gels comprising dispersed Trifarotene in the presence of microcapsules, the amount penetrated varies from 13.23% to 19.21%.

Thus, the microcapsules rightly make it possible to provide better penetration of the dispersed Trifarotene, and in this specific case from 2.7 to 4 times better in the presence of capsules compared with the reference gel with the dispersed active ingredient and not containing microcapsules.

In the presence of microcapsules containing 20% capric/caprylic acid triglycerides, i.e., gel VI/G-A1$_1$ of Example 3, the total amount of dispersed Trifarotene penetrated is comparable to that obtained with the reference cream in which Trifarotene is solubilized.

According to FIG. 2, the dispersed Trifarotene release profile is very different from those obtained with the reference cream and with the gels containing microcapsules. In the case of the gels, this profile increases in rate in proportion to the amount of oil and thus to the amount of microcapsules.

According to FIG. 3, representing the AUCs at 8 hours corresponding to the shortest exposure times, the gel not containing microcapsules exhibits an exposure of the active ingredient in the skin which is significantly different from that obtained with the reference cream and with the gels containing microcapsules. On the other hand, the gels with microcapsules exhibit an equivalent skin exposure irrespective of the oil content: 5% or 20%. Only the gel with 5% oil in microcapsule form is significantly different from the gel not containing microcapsules.

According to FIG. 4, representing the AUCs at 24 hours corresponding to the longest exposure times, the gel not containing microcapsules exhibits an exposure of the active ingredient in the skin which is significantly different from that obtained with the reference cream and with the gels containing microcapsules. The gel containing the most oil in microcapsule form (20%) exhibits a skin exposure equivalent to that obtained with the reference cream in which the active ingredient is solubilized. The greater the amount of microcapsules and thus the amount of solvent, the greater the skin exposure at the longer exposure times.

Over long periods of time, therefore, a gel containing an active ingredient dispersed in the presence of microcapsules containing a solvent of the active ingredient makes it possible to obtain skin exposure equivalent to that of a formulation in which the same active ingredient is solubilized, while limiting skin exposure at the shortest exposure times. This has an advantage with irritating active ingredients, for instance retinoids and in particular Trifarotene.

This in vitro skin penetration study showed that the presence of microcapsules containing a fatty substance that is a solvent of the active ingredient makes it possible to obtain total penetrated amounts of Trifarotene equivalent to that of a reference formula in which this same active ingredient is solubilized.

Similarly, this study also shows that the presence of microcapsules containing a fatty substance that is a solvent of the active ingredient also makes it possible to clearly increase the total penetrated amount of Trifarotene dispersed in a composition of gel type.

Example 7: Solubility and Stability Data for Compound A2 in Various Fatty Substances and Compounds of Non-Volatile Organic Solvent Type The solubility and the stability of the active ingredient were evaluated by liquid chromatography coupled to a UV detector (HPLC-UV).

| INCI name (trade name) | Maximum or visual* solubility (% w/w) (AT) | Stability (3M) (AT/40° C.) |
|---|---|---|
| Dimethyl capramide (Spectrasolv DMDA) | 20-30* | NR |
| Diethylene glycol monoethyl ether (Transcutol HP) | 13.9 | Stable ** |
| Diisopropyl adipate (Schercemol Dia Ester) | <1.0* | NR |
| PPG-15 stearyl ether (Arlamol PS11E-LQ) | <1.0* | NR |
| Capric/caprylic acid triglycerides (Miglyol ® 812N) | <0.1* | NR |

** Appearance of coloring at AT and at 40° C.

Following the results of this solubility study, it is noted that dimethyl capramide and diethylene glycol monoethyl ether are suitable for solubilizing Compound A2.

Following these results, dimethyl capramide and diethylene glycol monoethyl ether are the preferred solvents selected to be inserted in the oily core in the microcapsules in the presence of capric/caprylic acid triglycerides.

Example 8: Examples of Compositions of Gel Type According to the Invention Containing the Compound (A2) Dispersed in the Presence of Lipid Microcapsules Produced from the Primary Emulsions of Example 1

In order to produce compositions of gel type VII/G-A2$_1$, VII/G-A2$_2$, V/G-A2$_1$ and VIII/G-A2$_1$ according to the invention, an amount of corresponding primary emulsion prepared according to Example 1 was taken and diluted in a gel base.

To obtain 100 grams of gel containing about 5% of microencapsulated oil, 17.784 grams of primary emulsion is added to a formulation containing 1% of dispersed micronized Compound A2 (gel VII/G-A21).

To obtain 100 grams of gel containing about 10% of microencapsulated oil, 35.855 grams of primary emulsion is added to a formulation containing 1% of dispersed micronized Compound A2 (gels VII/G-A22 and V/G-A21).

To obtain 100 grams of gel containing about 20% of microencapsulated oil, 71.71 grams of primary emulsion is added to a formulation containing 1% of dispersed micronized Compound A2 (gel VIII/G-A2$_1$).

Primary emulsion VII leads respectively to gel compositions VII/G-A2$_1$ and VII/G-A2$_2$, described in the table below.

Primary emulsions V and VIII lead respectively to gel compositions V/G-A2$_1$ and VIII/G-A2$_1$, described in the table below.

Examples of compositions of gel type obtained according to the invention are thus as follows:

| Ingredients | Composition (% w/w) | | | |
|---|---|---|---|---|
| | VII/G-A2$_1$ | VII/G-A2$_2$ | V/G-A2$_1$ | VIII/G-A2$_1$ |
| Micronized Compound A2 | 1 | 1 | 1 | 1 |
| Dimethyl capramide | 1 | 2 | — | — |
| Diethylene glycol monoethyl ether | — | — | — | 8 |
| Capric/caprylic acid triglycerides | 4 | 8 | 10 | 12 |
| Hydrogenated lecithin | 0.72 | 1.4 | 1.4 | 2.9 |
| Sodium acryloyldimethyltaurate copolymer/isohexadecane/polysorbate 80 | 4 | 4 | 4 | 4 |
| Benzoic acid | 0.1 | 0.1 | 0.1 | 0.1 |
| Potassium sorbate | 0.1 | 0.1 | 0.1 | 0.1 |
| Disodium edetate | 0.1 | 0.1 | 0.1 | 0.1 |
| Glycerol | 5 | 5 | 5 | 5 |
| Cyclomethicone | 1.5 | 1.5 | 1.5 | 1.5 |
| Citric acid (q.s. pH 5-6) | q.s. pH | q.s. pH | q.s. pH | q.s. pH |
| Purified water | q.s. 100 | q.s. 100 | q.s. 100 | q.s. 100 |

Example 9: Characterization of the Compositions of Example 8 of Gel Type According to the Invention, According to the Lipophilic Compound Used and the Percentage of Microencapsulated Lipophilic Mixture or Mixture of Lipophilic Nature In the present examples, the equipment that was used to produce the primary emulsions is the Magic LAB® (IKA).

The preferred dispersion mode for the hydrogenated lecithin in the presence of capric/caprylic acid triglycerides with dimethyl capramide or of diethylene glycol monoethyl ether is 100% in the aqueous phase.

The gel composition VII/G-A21 contains 1% of dispersed micronized Compound A2, in the presence of about 5% of microencapsulated oil.

| Primary emulsion/Oil | Characterizations | Results |
|---|---|---|
| Composition VII/G-A2$_1$ | | |
| VII/ Dimethyl capramide - capric/caprylic acid triglycerides | Macroscopic observation | White gel |
| | Microscopic observation | Capsules of micrometric size and presence of Compound A2 crystals |
| | pH | 4.85 |
| | Viscosity RV, S06, 10 rpm | 49,100 cP |

The gel compositions VII/G-A22 and V/G-A21 contain 1% of dispersed micronized Compound A2, in the presence of about 10% of microencapsulated lipophilic mixture or mixture of lipophilic nature.

| Primary emulsion/Oil | Characterizations | Results |
|---|---|---|
| Composition VII/G-A2$_2$ | | |
| VII/ Dimethyl capramide - capric/caprylic acid triglycerides | Macroscopic observation | White gel |
| | Microscopic observation | Capsules of micrometric size and presence of Compound A2 crystals |
| | pH | 4.90 |
| | Viscosity RV, S06, 10 rpm | 75,500 cP |
| Composition V/G-A2$_1$ | | |
| V/ Capric/caprylic acid triglycerides | Macroscopic observation | White gel |
| | Microscopic observation | Capsules of micrometric size and presence of Compound A2 crystals |
| | pH | 5.20 |
| | Viscosity RV, S06, 5 rpm | 135,000 cP |

The gel composition VIII/G-A21 contains 1% of dispersed micronized Compound A2, in the presence of about 20% of microencapsulated lipophilic mixture or mixture of lipophilic nature.

| Primary emulsion/Oil | Characterizations | Results |
|---|---|---|
| Composition VIII/G-A2$_1$ | | |
| VIII/ Diethylene glycol monoethyl ether - capric/caprylic acid triglycerides | Macroscopic observation | White gel |
| | Microscopic observation | Capsules of micrometric size and presence of Compound A2 crystals |
| | pH | 4.95 |
| | Viscosity RV, S07, 5 rpm | 230,000 cP |

These results show that it is possible to produce a gel containing a dispersed active ingredient, namely Compound A2, and containing microcapsules with a lipophilic mixture comprising a non-oily compound of non-volatile organic solvent type (diethylene glycol monoethyl ether).

Example 10: Stability Study of the Gels of Example 9 According to the Lipophilic Compound Used and According to the Percentage of Microencapsulated Lipophilic Mixture or Mixture of Lipophilic Nature Gel obtained from composition V/G-A2$_1$ of Example 8 (10% capric/caprylic acid triglycerides)

| Characterizations | Storage conditions | Stability at 3 months |
|---|---|---|
| Macroscopic appearance | T0 | White gel |
| | AT | IDEM T0 |
| | 4° C. | IDEM T0 |
| | 40° C. | IDEM T0 |
| Microscopic appearance | T0 | Capsules of micrometric size and presence of Compound A2 crystals |
| | AT | IDEM T0 |
| | 4° C. | IDEM T0 |
| | 40° C. | IDEM T0 |
| pH Viscosity RV, S06, 5 rpm | T0 | pH = 5.20 135,000 cP |
| | AT | pH = 5.43 66,200 cP |
| | 40° C. | pH = 5.36 55,200 cP |
| Compound A2 assay Rec %/LC | AT | 99.9% |
| | 40° C. | 99.4% |
| Conclusions | | Physically and chemically stable gel |

Gel Obtained from Composition VIII/G-A2$_1$ of Example 8 (8% Diethylene Glycol Monoethyl Ether/12% Capric/Caprylic Acid Triglycerides)

| Characterizations | Storage conditions | Stability at 3 months |
|---|---|---|
| Macroscopic appearance | T0 | White gel |
| | AT | IDEM T0 |
| | 4° C. | IDEM T0 |
| | 40° C. | IDEM T0 |
| Microscopic appearance | T0 | Capsules of micrometric size and presence of Compound A2 crystals |
| | AT | IDEM T0 |
| | 4° C. | IDEM T0 |
| | 40° C. | IDEM T0 |
| pH Viscosity RV, S07, 5 rpm | T0 | pH = 4.95 230,000 cP |
| | AT | pH = 5.04 200,000 cP |
| | 40° C. | pH = 5.10 200,000 cP |
| Compound A2 assay Rec %/LC | AT | 100.5 |
| | 40° C. | 99.7 |
| Conclusions | | Physically and chemically stable gel |

The results show that gels are obtained that are physically stable at three months at ambient temperature and at 40° C. in the presence of a dispersed active ingredient, namely Compound A2.

Gel VIII/G-A2$_1$ is physically stable without the problem of the appearance of coloring, after three months at ambient temperature and at 40° C., with diethylene glycol monoethyl ether in the oily core. This absence of coloring had not been obtained with a gel-type formulation in which Compound A2 was 1% solubilized.

Example 11: In Vitro Skin Penetration Study of Compound A2 Dispersed in Gel Formulations in the Presence of Microcapsules Produced According to Example 1

Study Conditions:

In this study, the formulations were applied for 24 hours to the skin surface. At the end of the application, Compound A2 is quantified in the various skin compartments: stratum corneum, epidermis, dermis, and receiving liquid according to a validated bioanalysis method performed by positive electrospray ionization tandem mass spectrometry, using a Xevo system (Waters). The quantification limit for Compound A2 is 2 ng/mL. The LC/MS/MS conditions developed made it possible to detect up to 0.1% of the dose applied in each compartment (dose not absorbed, stratum, epidermis, dermis, and receiving liquid).

The details of the skin application are given in the table below.

| Skin: 3 donors, 2 samples per donor | |
|---|---|
| Source | Whole human abdominal skin |
| Franz cells | 2 cm$^2$ |
| Receiving liquid volume | 7 mL |
| Barrier function | Evaluated by determination of insensible water loss, acceptable unless contraindication |

Reference gel containing 10,000 μg/g dispersed micronized Compound A$_2$
Gel no. V/G-A2$_1$ Example 8 containing 10,000 μg/g micronized Compound A$_2$ dispersed in the presence of 10% microencapsulated lipophilic compound (capric/caprylic acid triglycerides)
Gel no. VIII/G-A2$_1$ Example 8 containing 10,000 μg/g micronized Compound A$_2$ dispersed in the presence of 20% microencapsulated lipophilic mixture (8% diethylene glycol monoethyl ether/12% capric/caprylic acid triglycerides)

| Application | |
|---|---|
| Application | 5 mg/cm$^2$ |
| Amount of active ingredient applied | 47,750 to 52,417 ng/cm$^2$ |
| Number of cells per formulation | 6 |

-continued

| Skin: 3 donors, 2 samples per donor | |
|---|---|
| Numbers of donors per formulation | 3 |
| Exposure time | 24 h |
| | Sample assay |
| Washing of donor compartment and wiping | "Excess"/Dose not absorbed |
| First strip | |
| Stratum corneum (2-15 strips max) | Total skin |
| Epidermis | |
| Dermis | |
| Receiving liquid | Dose absorbed |
| | LC/MS analysis |
| Quantification limit | 2 ng/mL |

The reference gel formula is a gel containing 1% of micronized Compound A2 the base composition of which is identical to those of gels V/G-A2$_1$ and VIII/G-A2$_1$ of Example 8. The reference gel is free of microcapsules.

| Ingredients/INCI names | Composition (% w/w) |
|---|---|
| Micronized Compound A$_2$ | 1.0 |
| Sodium acryloyldimethyltaurate copolymer/isohexadecane/polysorbate 80 | 4.0 |
| Benzoic acid | 0.1 |
| Potassium sorbate | 0.1 |
| Disodium edetate | 0.1 |
| Glycerol | 5.0 |
| Cyclomethicone | 1.5 |
| Citric acid (q.s. pH 5-6) | q.s. pH |
| Purified water | q.s. 100 |

Figure 5:
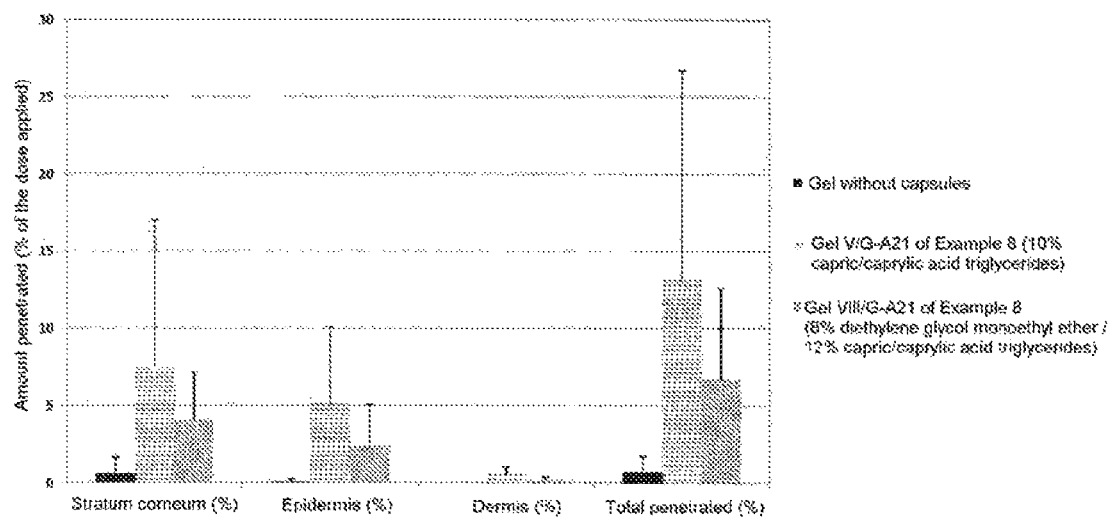
FIG. 5: Evaluation of the amount penetrated (% of the dose applied) in various skin compartments of Gels V/G-A21 and VIII/G-A21 of Example 8.

Results:

The results presented in FIG. 5 show the amount penetrated as a percentage of the dose applied (% of the dose applied) according to the various skin compartments.

Conclusions:

Irrespective of the formulation tested, the skin distribution of dispersed Compound A2 is essentially located in the stratum corneum and the epidermis, and more moderately in the dermis.

The total amount penetrated of Compound A2 in the gels containing Compound A2 dispersed in the presence of microcapsules is higher than the reference gel in which Compound A2 is dispersed alone without microcapsules.

With the reference gel comprising Compound A2 dispersed without microcapsules, the total amount penetrated is about 0.7%.

For the gels comprising Compound A2 dispersed in the presence of microcapsules, the total amount penetrated varies from 6.72% to 13.15%.

Thus, the microcapsules rightly make it possible to provide better penetration of dispersed Compound A2, and in this specific case from 9.6 to 18.8 times better in the presence of capsules compared with the reference gel with the dispersed active ingredient and not containing microcapsules.

The subject-matter of our invention, which announces the enhancement of the penetration of dispersed active ingredients by the use of lipid microcapsules for solubilizing the active ingredient during application to the skin, is clearly confirmed under the conditions of this study and with, by way of example, Compound A2.

This in vitro skin penetration study showed that the presence of microcapsules containing a lipophilic mixture that is a solvent of the active ingredient makes it possible to very significantly increase the total amount penetrated of Compound A2 dispersed in a gel relative to the same gel free of microcapsules.

It was also shown in this study that the nature of the oily core is a factor that influences the level of penetration of the active ingredient.

Example 12: Solubility Data for Compound A3 in Various Lipophilic Compounds or Compounds of Non-Volatile Organic Solvent Type and in Mixtures of these Compounds The solubility of the active ingredient was evaluated by liquid chromatography coupled to a UV detector (HPLC-UV).

| INCI name (trade name) | Maximum or visual* solubility (% w/w) (AT) |
|---|---|
| Dimethyl sulfoxide (Procipient DMSO) | >20%* |
| Diisopropyl adipate (Schercemol Dia Ester) | 0.02 |
| PPG-15 stearyl ether (Arlamol PS11E-LQ) | 0.01 |
| C12-15 alkyl lactate (Ceraphyl 41) | 0.04 |
| Capric/caprylic acid triglycerides (Miglyol ® 812N) | <detection limit |
| 10/90% Dimethyl sulfoxide/PPG-15 stearyl ether | 0.07 |
| 10/90% Dimethyl sulfoxide/Diisopropyl adipate | 0.38 |
| 10/90% Dimethyl sulfoxide/C12-15 alkyl lactate | 0.12 |
| 20/80% Dimethyl sulfoxide/Schercemol Dia Ester | 3.15 |
| 20/80% Dimethyl sulfoxide/C12-15 alkyl lactate | 0.74 |

Following the results of this solubility study, dimethyl sulfoxide is suitable for solubilizing Compound A3.

It is the compound of non-volatile organic type that is preferred and selected to be inserted in the oily core in the microcapsules in the presence of diisopropyl adipate.

Example 13: Examples of Compositions of Gel Type According to the Invention Containing Compound A3 Dispersed in the Presence of Lipid Microcapsules Produced from the Primary Emulsions of Example 1

In order to produce a composition of gel type IX/G-A3$_1$, according to the invention, an amount of corresponding primary emulsion prepared according to Example 1 was taken and diluted in a gel base.

To obtain 100 grams of gel containing about 10% of microencapsulated oil, 35.855 grams of primary emulsion is added to a formulation containing 3% of dispersed micronized Compound A3 (gel VII/G-A3$_1$).

Primary emulsion IX leads respectively to gel composition IX/G-A3$_1$ described in the table below.

An exemplary composition of gel type obtained according to the invention is thus as follows:

| Ingredients | Composition (% w/w) IX/G-A3$_1$ |
| --- | --- |
| Micronized Compound A3 | 3.0 |
| Dimethyl sulfoxide | 2.0 |
| Capric/caprylic acid triglycerides | 8.0 |
| Hydrogenated lecithin | 1.40 |
| Sodium acryloyldimethyltaurate copolymer/isohexadecane/polysorbate 80 | 4.0 |
| Methyl paraben | 0.2 |
| Propyl paraben | 0.1 |
| Butyl hydroxytoluene | 0.036 |
| Purified water | q.s. 100 |

Example 14: Characterization of the Compositions of Example 13 of Gel Type According to the Invention In the present example, the equipment that was used to produce the primary emulsion is the Magic LAB® (IKA).

The preferred dispersion mode for the hydrogenated lecithin with the dimethyl sulfoxide/diisopropyl adipate mixture is 100% in the aqueous phase.

Gel composition IX/G-A31 contains 3% of dispersed micronized Compound A3, in the presence of about 10% of microencapsulated lipophilic mixture.

| Primary emulsion/Oil | Characterizations | Results |
| --- | --- | --- |
| Composition IX/G-A1$_1$ | | |
| IX/ Dimethyl sulfoxide - capric/caprylic acid triglycerides | Macroscopic observation | White gel |
| | Microscopic observation | Capsules of micrometric size and presence of Compound A3 crystals |
| | pH | 5.92 |

These results show that it is possible to produce a gel containing a dispersed active ingredient, namely Compound A3, and containing microcapsules with a lipophilic mixture comprising a non-oily compound of non-volatile organic solvent type (dimethyl sulfoxide).

The invention claimed is:

1. A pharmaceutical composition comprising at least one retinoid dispersed in a pharmaceutically acceptable carrier and lipid microcapsules,
 wherein:
  the lipid microcapsules have a mean size from 1 μm to 80 μm and comprise an oily internal phase and a nonpolymeric shell obtained from at least one lipid compound selected from amphiphilic lipids, and
  the at least one retinoid is outside the lipid microcapsules and exhibits chemical stability for at least three months at ambient temperature and 40° C.

2. The composition according to claim 1, wherein the retinoid comprises Trifarotene.

3. The composition according to claim 1, wherein the lipid microcapsules are dispersed in an aqueous phase.

4. The composition according to claim 1, wherein the at least one lipid compound that forms the nonpolymeric shell is a hydrogenated lecithin with a weight amount of phosphatidylcholine greater than 85%.

5. The composition according to claim 4, wherein the at least one lipid compound is present in an amount of from 0.01% to 10% by weight relative to the total weight of the composition.

6. The composition according to claim 1, wherein the microcapsules are free of co-surfactant, of volatile organic solvent, or of polymer.

7. The composition according to claim 1, wherein the oily internal phase of the microcapsules comprises at least one fatty substance that is liquid or semiliquid at ambient temperature selected from the group consisting of polyethoxylated fatty acids, triglycerides, oils comprising the triglycerides, fatty acid esters, and polyethylene glycol ethers.

8. The composition according to claim 1, wherein the oily internal phase comprises at least one fatty substance that is liquid or semiliquid at ambient temperature comprising triglycerides, fatty acid esters, polyethylene glycol ethers, or dimethyl isosorbide.

9. A composition comprising:
 (a) 0.001% to 1% by weight of a retinoid dispersed in a pharmaceutically acceptable carrier, relative to the total weight of the composition, and
 (b) lipid microcapsules having a mean size from 1 m to 80 m and comprising:
  (i) 0.1% to 5% of a nonpolymeric shell comprising hydrogenated lecithin with a hydrogenated phosphatidylcholine content of greater than 85%; and
  (ii) 1% to 30% of an internal oily phase comprising oily and optionally non-oily fatty substances;
 wherein the retinoid is outside of the lipid microcapsules and exhibits chemical stability for at least three months at ambient temperature and 40° C.

10. The composition according to claim 1, wherein the pharmaceutically acceptable carrier is a gel.

11. The composition according to claim 1, wherein the pharmaceutically acceptable carrier is a solution.

12. The composition according to claim 1, wherein the pharmaceutically acceptable carrier is a cream.

13. The composition according to claim 1, wherein the composition is in a form suitable for topical administration.

14. The composition according to claim 1, wherein the composition is formulated for use as a medicinal product.

15. A process for preparing the composition according to claim 1, the process comprising:
 (i) preparing a primary emulsion by:
  a) preparing an oily phase heated to 75° C.,
  b) dispersing a lipid compound in an aqueous phase, heated to 75° C.,
  c) incorporating the oily phase onto the aqueous phase with stirring at a speed of less than 16,000 rpm to form a mixture, and
  d) allowing the mixture to circulate until it returns to ambient temperature; and
 (ii) incorporating the primary emulsion into the pharmaceutically acceptable carrier comprising the at least one dispersed retinoid.

16. The composition according claim 1, wherein the lipid microcapsules have a mean size is from 1 μm to 50 μm.

17. The composition according claim 1, wherein the lipid microcapsules have a mean size is from 1 μm to 20 μm.

18. The composition according to claim 5, wherein the at least one lipid compound is present in an amount from 0.05% to 5% by weight.

19. The composition according to claim 5, wherein the at least one lipid compound is present in an amount from 0.01% to 1% by weight.

20. The composition according to claim 9, wherein the retinoid comprises Trifarotene.

21. The composition according to claim 9, wherein the oily and optionally non-oily fatty substances are selected from the group consisting of triglycerides, fatty acid esters, polyethylene glycol ethers, and dimethyl isosorbide.

22. The process according to claim 15, wherein the lipid compound is hydrogenated lecithin.

23. The composition of claim 1, wherein the retinoid is Trifarotene.

24. The composition according to claim 1, wherein the oily internal phase of the microcapsules comprises dimethyl capramide, diethylene glycol monoethyl ether, or a combination thereof.

25. The composition according to claim 2, wherein the pharmaceutically acceptable carrier is a gel.

26. The composition according to claim 1, wherein the at least one retinoid is not present in the lipid microcapsules.

\* \* \* \* \*